(12) United States Patent
Bouton

(10) Patent No.: US 7,591,792 B2
(45) Date of Patent: Sep. 22, 2009

(54) ELECTROMAGNETIC SENSORS FOR BIOLOGICAL TISSUE APPLICATIONS AND METHODS FOR THEIR USE

(75) Inventor: Chad Edward Bouton, Delaware, OH (US)

(73) Assignee: Medrad, Inc., Indianola, PA (US)

( * ) Notice: Subject to any disclaimer, the term of this patent is extended or adjusted under 35 U.S.C. 154(b) by 802 days.

(21) Appl. No.: 10/205,775

(22) Filed: Jul. 26, 2002

(65) Prior Publication Data
US 2003/0036674 A1 Feb. 20, 2003

Related U.S. Application Data

(60) Provisional application No. 60/308,012, filed on Jul. 26, 2001.

(51) Int. Cl.
*A61B 5/117* (2006.01)
*A61B 5/103* (2006.01)

(52) U.S. Cl. .............. 600/587; 600/547; 600/430; 600/382; 600/384; 600/393; 604/141; 604/142; 604/143; 604/145; 604/146; 604/147; 604/148; 604/149; 604/150; 604/151; 343/718; 343/757

(58) Field of Classification Search .......... 600/547, 600/407, 382, 384, 393, 587, 430; 604/141–151; 343/718, 757, 700
See application file for complete search history.

(56) References Cited

U.S. PATENT DOCUMENTS 3,779,079 A 12/1973 Snook (Continued)

FOREIGN PATENT DOCUMENTS

DE 2921856 4/1982

(Continued)

OTHER PUBLICATIONS

Carr, K. L., "Use of Gallium Arsenide in Medical Applications," IEEE Gallium Arsenide Integrated Circuits (GAAS IC) Symposium, Vol. SYMP 17, pp. 10-13, New York (Oct. 29, 1995).

(Continued)

*Primary Examiner*—Brian Casler
*Assistant Examiner*—Baisakhi Roy
(74) *Attorney, Agent, or Firm*—Jill Denesvich; Henry E. Bartony, Jr.; Gregory L. Bradley

(57) ABSTRACT

Tissue sensors house one or more sensor elements. Each element has a housing mounted substrate and a superstrate with a planar antenna between. A transitional periphery (TP) of a superstrate outer surface interconnects a base to a plateau. At least some of the TP has a generally smooth transition. Plural elements are spaced by the housing. Alternately, the superstrate TP is flat, the housing extends to the outer superstrate surface and a shield surrounds the element. The housing is flush with or recessed below the superstrate and defines a TP between the housing and superstrate. A method converts a reference signal to complex form; plots it in a complex plane as a reference point (RP); converts a measurement signal to complex form; plots it in the complex plane as a measurement point (MP); determine a complex distance between the MP and the RP; and compares complex distance to a threshold.

58 Claims, 26 Drawing Sheets

U.S. PATENT DOCUMENTS

| | | | |
|---|---|---|---|
| 3,951,136 A | 4/1976 | Wall | |
| 4,010,749 A | 3/1977 | Shaw | |
| 4,240,445 A | 12/1980 | Iskander et al. | |
| 4,329,689 A | 5/1982 | Yee | |
| 4,378,808 A | 4/1983 | Lichtenstein | |
| 4,488,559 A | 12/1984 | Iskander | |
| 4,572,182 A | 2/1986 | Royse | |
| 4,575,705 A | 3/1986 | Gotcher | |
| 4,589,422 A | 5/1986 | James et al. | |
| 4,641,659 A | 2/1987 | Sepponen | |
| 4,647,281 A * | 3/1987 | Carr | 604/503 |
| 4,648,869 A | 3/1987 | Bobo, Jr. | |
| 4,653,501 A | 3/1987 | Cartmell et al. | |
| 4,667,679 A | 5/1987 | Sahota | |
| 4,690,149 A | 9/1987 | Ko | |
| 4,702,262 A | 10/1987 | Anderson | |
| 4,816,019 A | 3/1989 | Kamen | |
| 4,819,648 A | 4/1989 | Ko | |
| 4,877,034 A | 10/1989 | Atkins et al. | |
| 4,923,442 A | 5/1990 | Seagall et al. | |
| 4,959,050 A | 9/1990 | Bobo, Jr. | |
| 4,971,068 A | 11/1990 | Sahi | |
| 5,001,436 A | 3/1991 | Scot et al. | |
| 5,026,348 A | 6/1991 | Venegas | |
| 5,200,756 A * | 4/1993 | Feller | 343/700 MS |
| 5,334,141 A | 8/1994 | Carr et al. | |
| 5,334,941 A * | 8/1994 | King | 324/637 |
| 5,769,784 A | 6/1998 | Barnett et al. | |
| 5,859,614 A * | 1/1999 | Paolella et al. | 343/700 MS |
| 5,861,019 A | 1/1999 | Sun et al. | |
| 5,947,910 A | 9/1999 | Zimmet | |
| 5,954,668 A | 9/1999 | Uber, III et al. | |
| 5,957,950 A | 9/1999 | Mockros et al. | |
| 5,964,703 A | 10/1999 | Goodman et al. | |
| 5,990,472 A * | 11/1999 | Rinne | 250/214.1 |
| 5,995,863 A | 11/1999 | Farace et al. | |
| 6,026,173 A | 2/2000 | Svenson et al. | |
| 6,047,215 A | 4/2000 | McClure et al. | |
| 6,061,589 A | 5/2000 | Bridges et al. | |
| 6,166,692 A * | 12/2000 | Nalbandian et al. | 343/700 MS |
| 6,208,903 B1 | 3/2001 | Richards et al. | |
| 6,233,479 B1 | 5/2001 | Haddad et al. | |
| 6,264,611 B1 * | 7/2001 | Ishikawa et al. | 600/486 |
| 6,300,906 B1 * | 10/2001 | Rawnick et al. | 343/700 MS |
| 6,332,087 B1 | 12/2001 | Svenson et al. | |
| 6,375,624 B1 | 4/2002 | Uber, III et al. | |
| 6,385,473 B1 * | 5/2002 | Haines et al. | 600/393 |
| 6,408,204 B1 | 6/2002 | Hirschman | |
| 6,425,878 B1 * | 7/2002 | Shekalim | 604/65 |
| 6,459,931 B1 | 10/2002 | Hirschman | |
| 6,537,232 B1 * | 3/2003 | Kucharczyk et al. | 600/561 |
| 6,575,931 B1 * | 6/2003 | Ponzi | 604/95.01 |
| 6,579,498 B1 * | 6/2003 | Eglise | 422/82.05 |
| 2001/0050651 A1 * | 12/2001 | Grangeat et al. | 343/767 |
| 2002/0040193 A1 | 4/2002 | Hirschman | |
| 2002/0172323 A1 | 11/2002 | Karellas et al. | |
| 2003/0004433 A1 | 1/2003 | Hirschman | |
| 2003/0036713 A1 | 2/2003 | Bouton et al. | |
| 2003/0117321 A1 * | 6/2003 | Furse et al. | 343/700 MS |

FOREIGN PATENT DOCUMENTS

| | | |
|---|---|---|
| DE | 40 07 587 A1 | 9/1991 |
| FR | 2686739 | 7/1993 |
| FR | 2703872 | 10/1994 |
| GB | 2 251 080 A | 6/1992 |
| JP | 01249071 | 10/1989 |
| JP | 11-57001 | 3/1999 |
| WO | WO 99/26685 | 6/1999 |
| WO | WO 99/26686 | 6/1999 |
| WO | WO 99/29356 | 6/1999 |
| WO | WO 01/08729 | 2/2001 |
| WO | WO 03/009753 | 2/2003 |

OTHER PUBLICATIONS

Shaeffer, J. et al., "Early Detection of Extravasation of Radiographic Contrast Medium," Radiology, vol. 184, No. 1, pp. 141-144 (Jul. 1992).

Shaeffer, J., "Detection of Extravasation of Antineoplastic Drugs by Microwave Radiometry," Cancer Letters, 31, pp. 185-291 (1986).

"MMIC Receiver for Water-Vapor Radiometer," NASA Tech. Briefs, 34, (Sep. 1993).

Montreuil and Nachman, "Multiangle Method for Temperature Measurement of Biological Tissues by Microwave Radiometry," IEEE Transactions on Microwave Theory and Techniques, vol. 39, No. 7, pp. 1235-1238 (Jul. 1991).

Lin, J. C. et al., "Microwave Imaging of Cerebral Edema," Proceedings of the IEEE, vol. 70, No. 5, pp. 523-524 (May 1982).

Kramer, G. G. et al., "Dielectric Measurement of Cerebral Water Content Using a Network Analyzer," Neurological Research, vol. 14, No. 3, pp. 255-258 (Sep. 1992).

Ling, Geoffrey S. F. et al., "Diagnosis of Subdural and Intraparenchymal Intracranial Hemorrhage Using a Microwave Based Detector," Digitization of the Battlespace V and Battlefield Biomedical Technologies II, vol. 4037, pp. 212-217 (Apr. 24, 2000).

Behari, J., et al., "Dielectric Permittivity of Biological Tissues in the Microwave Frequency Range," Proceedings of the SPIE- The International Society for Optical Engineering, Advanced Microwave and Millimeter-Wave Detectors, vol. 2275, pp. 301-308, San Diego, CA (Jul. 25-26, 1994).

Arkin, et al., "Recent Developments in Modeling Heat Transfer in Blood Perfused Tissues," IEEE Transactions on Biomedical Engineering, vol. 41, No. 2, pp. 97-107 (Feb. 1994).

Harris and Von Maltzahn, "Infusion Line Model for the Detection of Infiltration Extravasation and Other Fluid Flow Faults," IEEE Transactions on Biomedical Engineering, vol. 40, No. 2, pp. 154-162 (Feb. 1993).

International Search Report for PCT Application No. PCT/US00/20112.

International Search Report for PCT Application No. PCT/US02/23925.

U.S. Appl. No. 10/060,561, filed Jan. 30, 2002.

Andreuccetti D et al; "High Permittivity Patch Radiator for Single and Multi-Element Hyperthermia Applicators"; IEEE Transactions on Biomedical Engineering; Jul. 1, 1993; pp. 711-715; vol. 40 No. 7; IEEE Inc.; New York.

Lee E R et al; "Body Conformable 915 MHz Microstrip Array Applicators for Large Surface Area Hyperthermia"; IEEE Transactions on Biomedical Engineering; May 1, 1992; pp. 470-483; vol. 39 No. 5; IEEE Inc.; New York.

M. Kent; Hand-Held Instrument for Fat/Water Determination in Whole Fish; Research Paper from Distell Website—/www.distell.com/index.php?exe=products:fish%20fat%20meter:research%20paper:—Distell, West Lothian, Scotland.

European Search Report from counterpart European Patent Application No. 06000717.6.

* cited by examiner

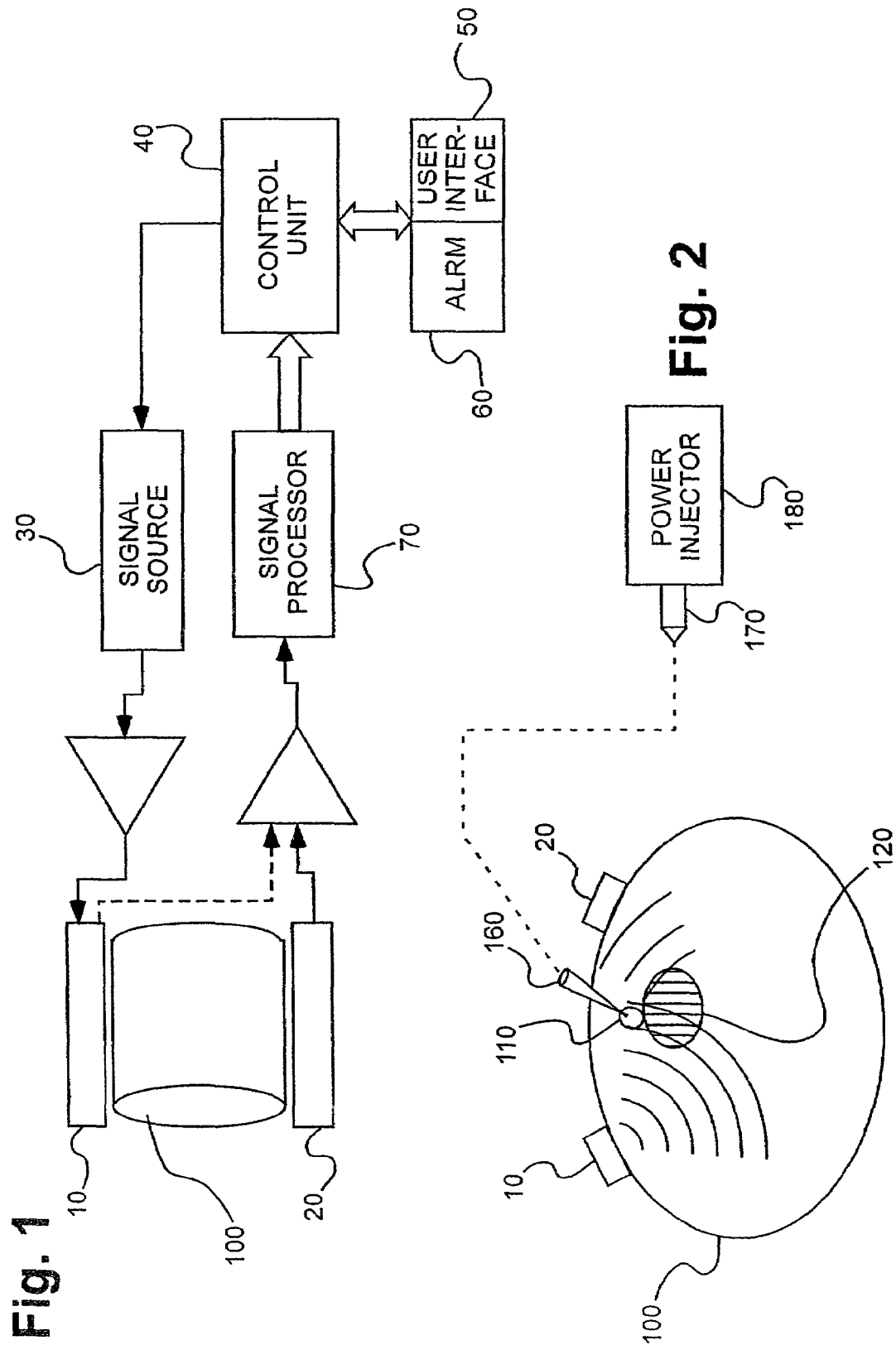

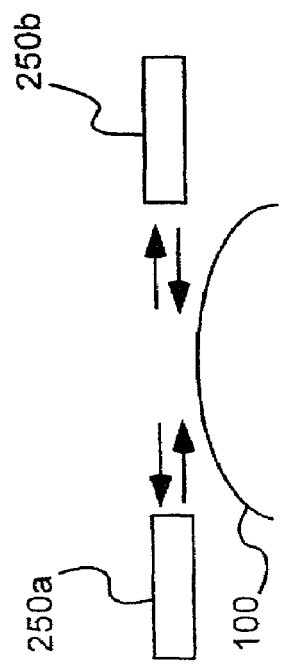
Fig. 4B
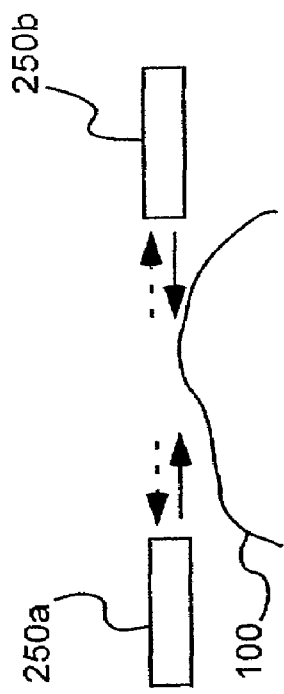
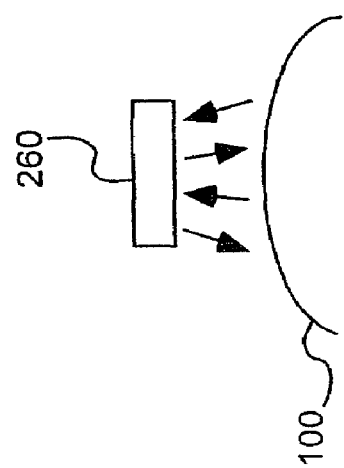
Fig. 4C
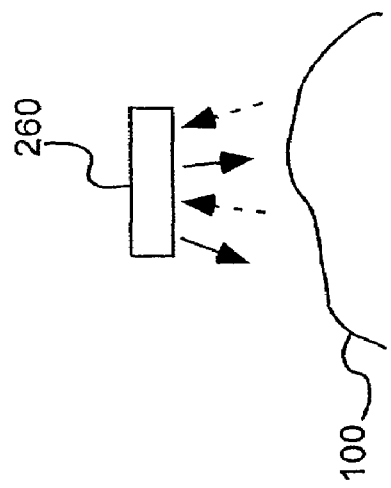

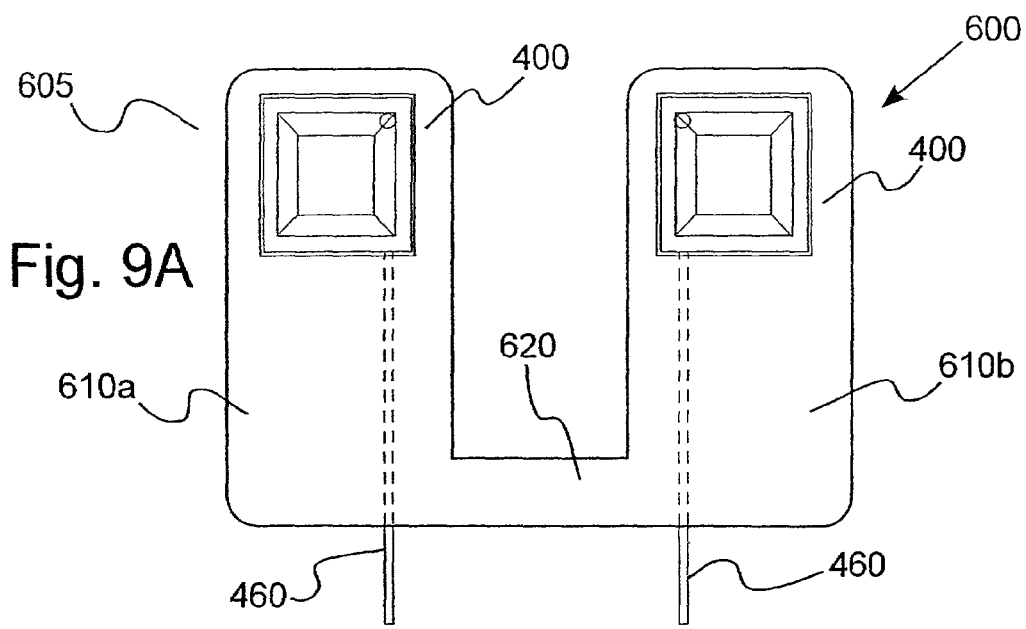
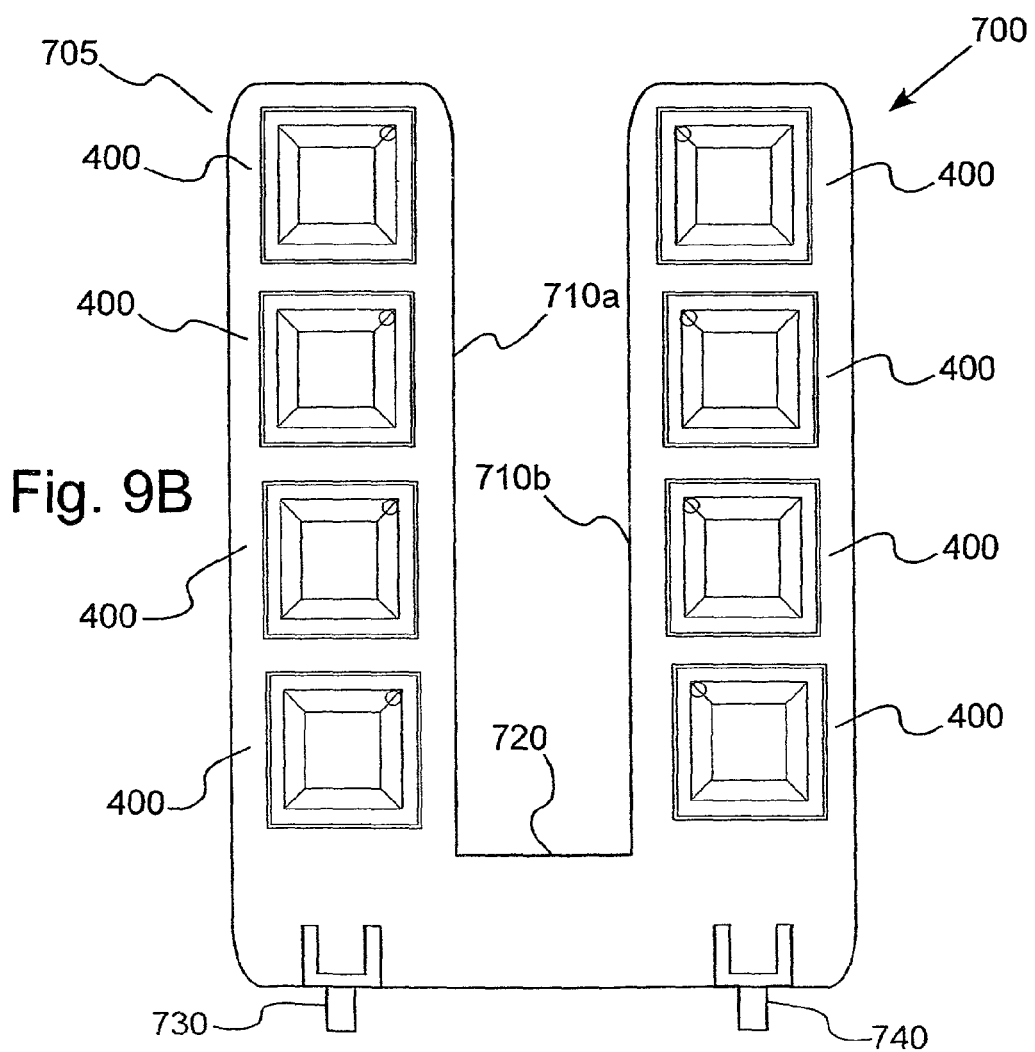

Fig. 19A
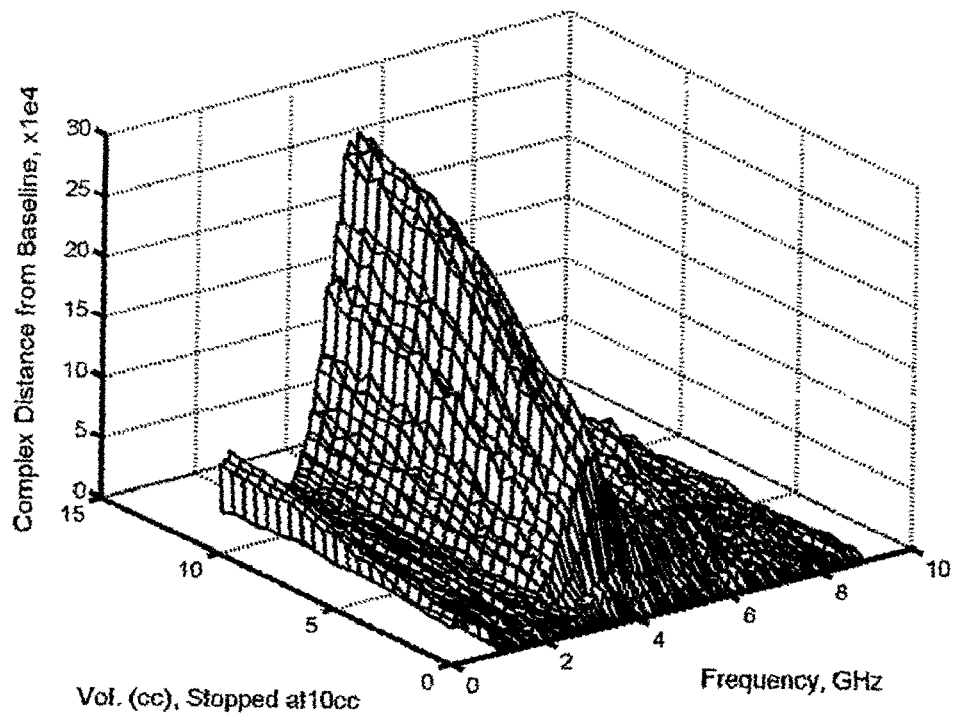
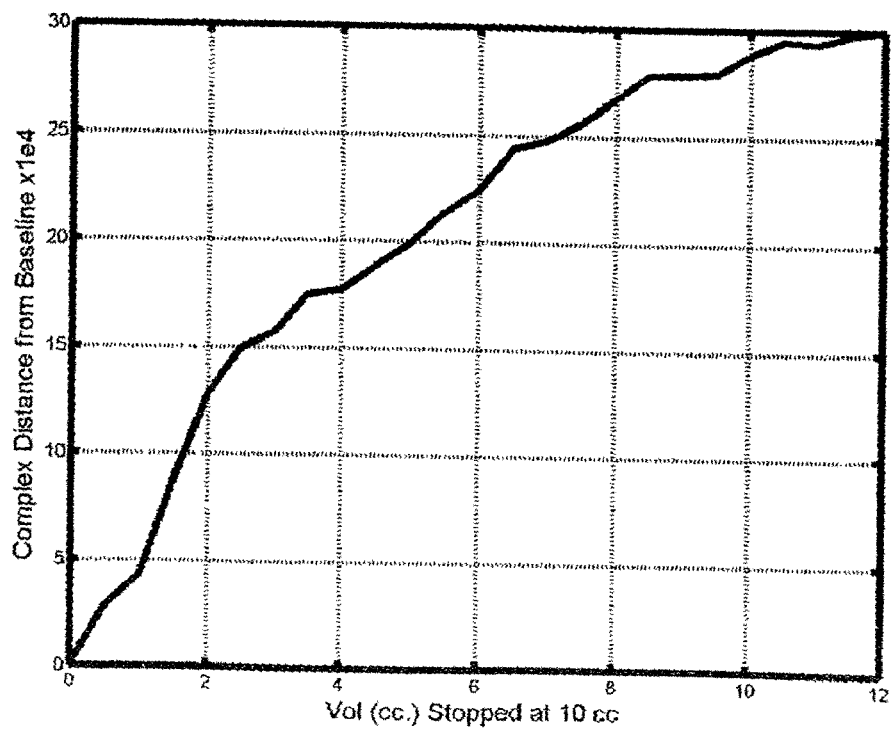

Fig. 19B
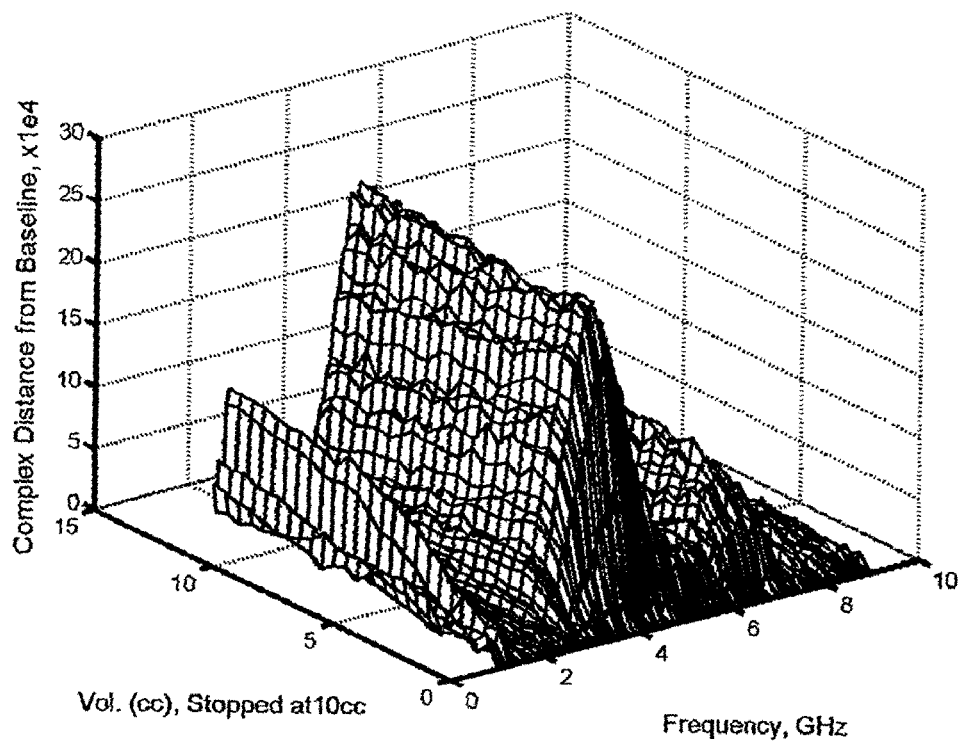
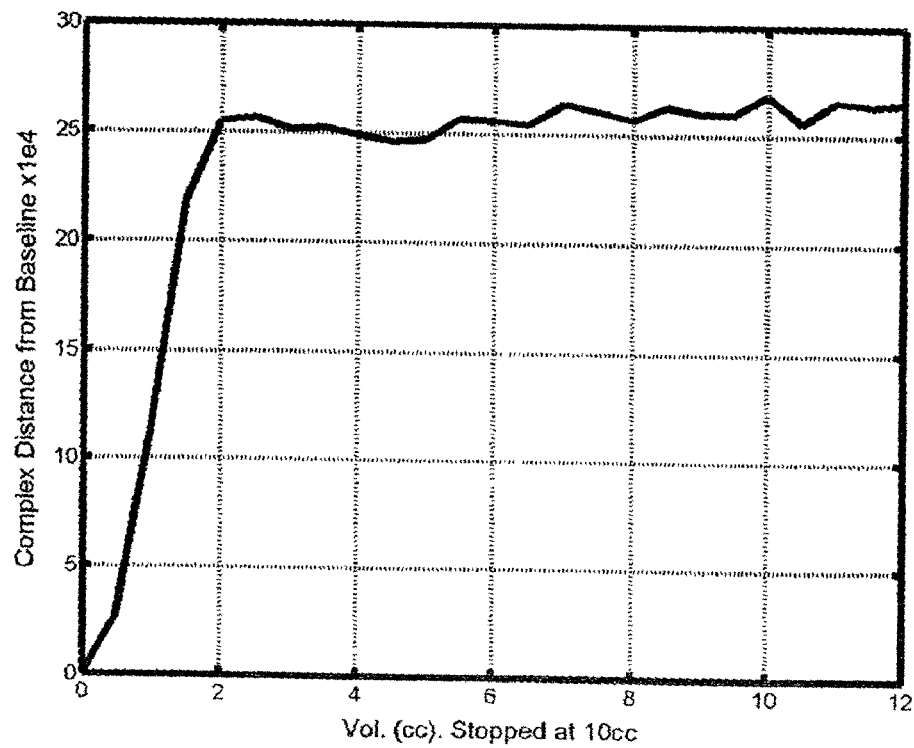

Fig. 19C
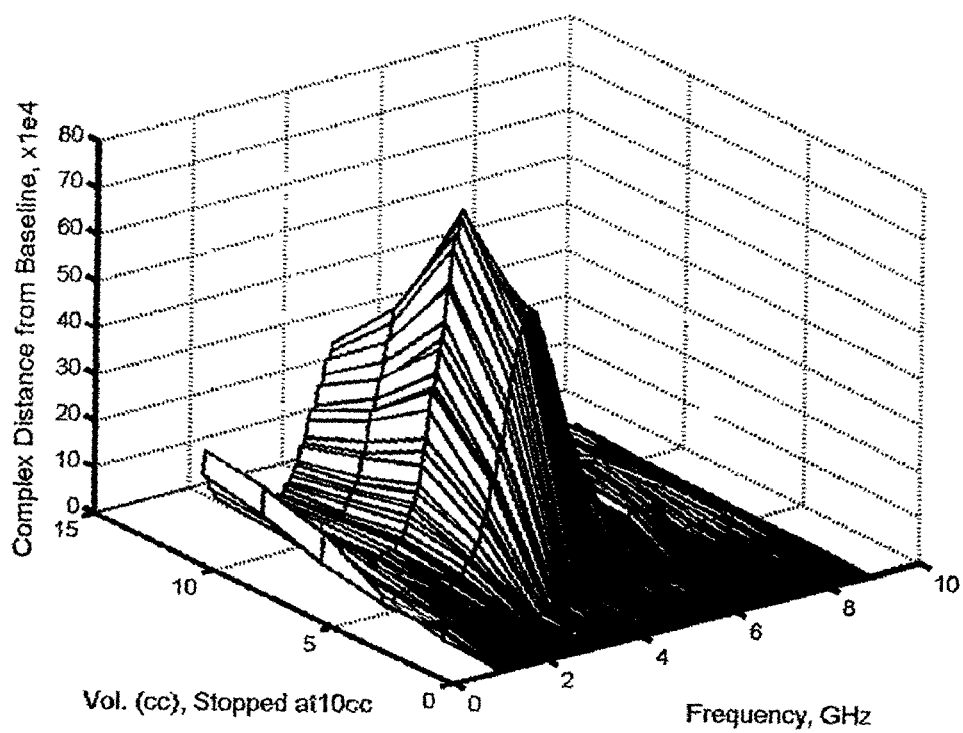
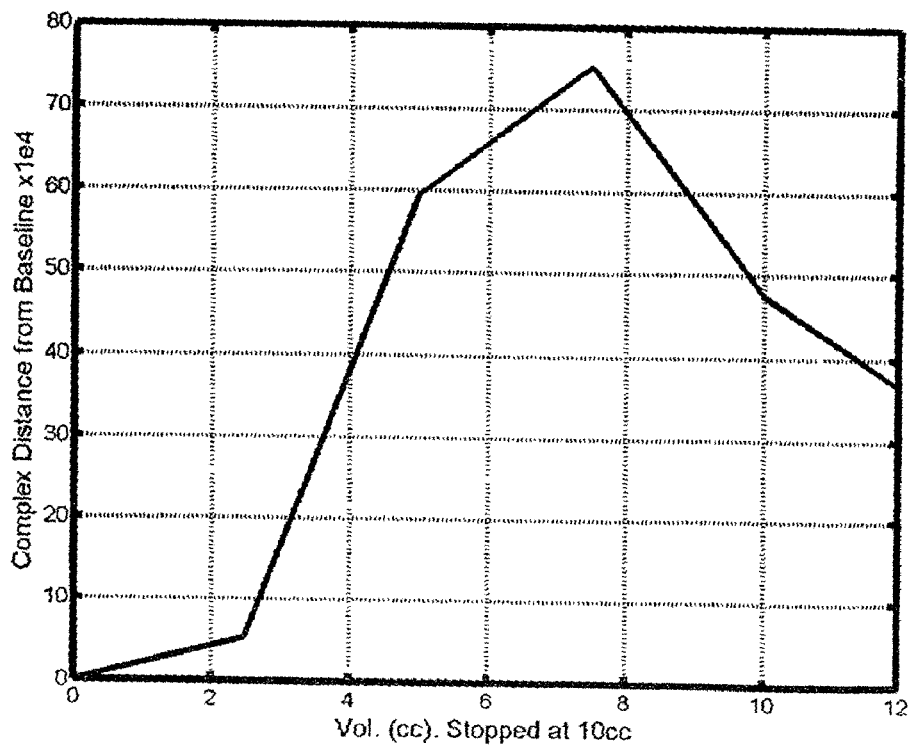

ELECTROMAGNETIC SENSORS FOR BIOLOGICAL TISSUE APPLICATIONS AND METHODS FOR THEIR USE

CROSS-REFERENCE TO RELATED APPLICATIONS

This application claims the benefit of U.S. Provisional Patent Application Ser. No. 60/308,012, filed Jul. 26, 2001, the disclosure of which is incorporated herein by reference. This application is related to an application (Express Mail Label No. EL886755793US) filed on even date herewith, entitled DETECTION OF FLUIDS IN TISSUE, also claiming priority to U.S. Provisional Patent Application Ser. No.60/308,012, filed Jul. 26, 2001, the disclosure of which is also incorporated herein by reference.

BACKGROUND OF THE INVENTION

The present invention relates in general to the detection of fluid and other materials in biological tissues and, more particularly, to electromagnetic sensors and methods of using those sensors for the detection of fluid and other materials in tissues. While the present invention is generally applicable to sensing of bodily or injected fluid levels or the presence of other foreign materials, such as tumors, in tissues, as well as microwave imaging and the like, it will be described herein primarily with reference to extravasation for which it is particularly applicable and initially being utilized.

Sensing changed, elevated or abnormal fluid levels in living tissues is often important to patient treatment. One example of abnormal fluid levels in tissue is edema, i.e., an abnormal accumulation of watery fluid in the intercellular spaces of connective tissue. Edematous tissues are swollen and, when punctured, secrete a thin incoagulable fluid. Edema is most frequently a symptom of disease rather than a disease in itself, and it may have a number of causes, most of which can be traced back to gross variations in the physiological mechanisms that normally maintain a constant water balance in the cells, tissues, and blood. Among the causes may be diseases of the kidneys, heart, veins, or lymphatic system; malnutrition; or allergic reactions. Abnormal fluid levels also arise in tissues due to hemorrhage or the discharge of blood from blood vessels with the collection and clotting of blood in tissues leading to hematomas. Hematomas normally are the result of injury.

In addition to the accumulation of body fluids, elevated fluid levels in tissues can arise as a result of introduction of a fluid into the body, for example, during an injection procedure. In that regard, in many medical diagnostic and therapeutic procedures, a physician or other person injects fluid into a patient's blood vessels. Moreover, in recent years, a number of injector-actuated syringes and powered injectors for pressurized injection of contrast medium in procedures such as angiography, computed tomography, ultrasound and nuclear magnetic resonance/magnetic resonance imaging (NMR/MRI) have been developed.

Extravasation or infiltration is the accidental infusion or leakage of an injection fluid, such as a contrast medium or a therapeutic agent, into tissue surrounding a blood vessel rather than into the blood vessel itself. Extravasation can be caused, for example, by rupture or dissection of fragile vasculature, valve disease, inappropriate needle placement, or patient movement resulting in the infusing needle being pulled from the intended vessel or causing the needle to be pushed through the wall of the vessel. High injection pressures and/or rates of some modern procedures can increase the risk of extravasation. In computed tomography, for example, contrast injection flow rates can be in the range of 0.1 to 10 ml/s.

Extravasation can cause serious injury to patients. In that regard, certain injection fluids such as contrast media or chemotherapy drugs can be toxic to tissue. It is, therefore, very important when performing fluid injections to detect extravasation as soon as possible and discontinue the injection upon detection.

Several extravasation detection techniques are known in the art. Two simple and very useful techniques for detecting extravasation are palpation of the patient in the vicinity of the injection site and simple visual observation of the vicinity of the injection site by a trained health care provider. In the palpation technique, the health care provider manually senses swelling of tissue near the injection resulting from extravasation. By visual observation, it is also sometimes possible to observe directly any swelling of the skin in the vicinity of an injection site resulting from extravasation.

In addition to palpation and observation, there are a number of automatic methods of detecting extravasation that include automatically triggering an alarm condition upon detection. For example, U.S. Pat. No. 4,647,281 discloses subcutaneous temperature sensing of extravasation to trigger such an alarm. In this method of extravasation detection, an antenna and a microwave radiometer instantaneously measure the temperature of the subcutaneous tissue at the site where fluid is injected. An algorithm periodically determines the temperature difference between tissue and injected fluid, and compares the difference to a fixed threshold. An alarm processor uses the comparison to determine an alarm condition.

U.S. Pat. No. 5,334,141 discloses a microwave extravasation detection system employing a reusable microwave antenna and a disposable attachment element for releasably securing the microwave antenna to a patient's skin over an injection site. The attachment element holds the antenna in intimate contact with the patient's skin to optimize microwave transfer therebetween, while shielding the antenna from environmental noise signals. U.S. Pat. No. 5,954,668 also discloses use of a microwave antenna to sense temperature of tissue to detect extravasation.

In addition to microwave radiometry for the detection of extravasation as described above, radiometry has also been proposed for the detection of pulmonary edema as described in U.S. Pat. No. 4,488,559. U.S. Pat. No. 4,240,445 discloses detection of pulmonary edema via transmitting electromagnetic energy through a transmission line coupled to tissue. U.S. Pat. No. 4,690,149 discloses detection of brain edema via impedance changes detected by a sensor. A proposed method of detection of brain edema is also disclosed in U.S. Pat. No. 6,233,479, in which a measured signal from a microwave antenna is compared to stored characteristic hematoma signals from hematomas of different thicknesses and a predetermined threshold value which can be used for judging whether or not a hematoma signal from an actual patient represents a real blood pool or not.

Microwave energy has also been used for the detection of tumors in living tissue as described in U.S. Pat. No. 6,061,589. Unlike the passive measurements in microwave radiometry, U.S. Pat. No. 6,061,589 disclosed transmission of electromagnetic energy into the body (breast tissue) using a microwave antenna with collection and measurement of a resultant signal. In that regard, U.S. Pat. No. 6,061,589 describes a microwave antenna to detect incipient tumors in accordance with differences in relative dielectric characteristics. Electromagnetic energy in the microwave frequency range is applied to a discrete volume in the tissue and scattered signal returns are collected. The irradiated location is shifted or changed in a predetermined scanning pattern. The returned signals are processed to detect anomalies indicative of the present of a tumor.

Likewise, microwave energy has been proposed for use in water content mapping in human tissue as described in U.S. Pat. No. 5,995,863. Microwave energy has also been used in non-invasive tomographic spectroscopy imaging. See U.S. Pat. Nos. 6,332,087 and 6,026,173.

Microwave energy has also further been used to measure the fat content in nonliving organic tissue. For example, M. Kent, "Hand Held Fat/Water Determination", (1993), available at www.distell.com/products/papers/paper2.htm, discloses a microstrip transmission line type sensor for such a determination. In general, the fat content of pelagic and other fatty species of fish is proportion to water content. The dielectric properties of the fish depend on the water content. In the device of Kent, changes in the transmission properties of the microstrip transmission line held against the fish were calibrated against water content. Through simulations it was found that the present invention is significantly more sensitive to changes within biological tissue due to the fact that it relies on the tissue as the transmission path rather than a transmission line. In an open transmission line type sensor, a significant fraction of the transmitted energy travels through the transmission line itself and is significantly less impacted by changes in the underlying tissue. In the present invention, a large fraction of the energy travels through the tissue and therefore changes in the tissue path will impact the signal more drastically.

It is very desirable to develop improved sensors and methods for their use in detecting elevated or otherwise abnormal levels of fluids in living tissue, for example, as the result of edema, hematoma or extravasation. Such sensors and methods would also be desirable for detecting the presence of other materials, such as tumors, in living tissue as well as for microwave imaging and other like applications.

SUMMARY OF THE INVENTION

In accordance with one aspect of the present invention, a sensor element for injecting and/or receiving electromagnetic waves into body tissue comprises a housing with a substrate mounted within the housing. A superstrate is mounted to the substrate and has a base facing the substrate and an outer surface extending away from the substrate and having a transitional periphery interconnecting the base to an outer surface plateau extending over at least a central portion of the superstrate. A generally planar antenna element is accommodated by and mounted between the substrate and the superstrate, wherein at least a portion of said transitional periphery of the outer surface of the superstrate has a generally smooth transition from the base to the surface plateau. The smooth transition reduces and substantially eliminates air pockets where the superstrate contacts tissue to be sensed and thereby improves signal coupling and resulting measurements. The sensor element can be used for transmitting and/or receiving electromagnetic wave energy.

The transitional periphery can be generally linear so that the outer surface forms a truncated pyramid or curvilinear so that it is nearly undetectable in plan view. The housing can be formed of a variety of materials but preferably is a resilient material such as polyurethane. The planar antenna element can be substantially any shape including rectangular and circular. In an illustrative embodiment, the planar antenna element comprises a rectangular electrically conductive patch.

In this embodiment, the planar antenna element, more particularly, is square and is electrically contacted adjacent a corner of the element to generate circularly polarized electromagnetic wave signals. To somewhat control electromagnetic wave directionality, only a portion of the transitional periphery of the outer surface of the superstrate can have a generally smooth transition from the base to the surface plateau so that electromagnetic waves are directed toward that portion for both transmission and reception. The sensor element may further comprise an electrically conductive shield around at least a portion of the substrate to form an electrically conductive cavity. It is currently preferred to match a resonance mode of the antenna element to a resonance mode of the cavity so that the antenna element and the cavity resonant together. When the antenna element and the cavity are rectangular, the resonance mode of the antenna element corresponds to a diagonal measurement of the antenna element and the resonance mode of the cavity corresponds to a side dimension of the cavity.

The sensor element can be constructed to have the antenna element and the cavity be congruent squares. For economy sake, it may be beneficial to be able to reuse the antenna element so that the antenna element may be mounted to the substrate and the superstrate may be removably mounted to the substrate and disposable. The outer surface of the superstrate may include adhesive for securing the sensor element to the body tissue, for example by double-sided tape. The substrate and the superstrate may be constructed of a high permittivity, low loss material, for example, a ceramic material such as magnesium calcium titanium dioxide ($MgCaTiO_2$). To improve coupling electromagnetic waves into tissue to be sensed, the superstrate may comprise a material with an intrinsic impedance substantially the same as the surface impedance of the tissue into which electromagnetic waves are to be injected and/or from which electromagnetic waves are to be received. The base of the superstrate can include an indentation sized to receive the generally planar antenna element and/or can be formed to accommodate an electrical connection to the generally planar antenna element.

In accordance with another aspect of the present invention, a sensor comprises at least two sensor elements with each sensor element comprising a substrate and a superstrate. The superstrate is mounted to the substrate and has a base facing the substrate and an outer surface extending away from the substrate with the outer surface having a transitional periphery interconnecting the base to an outer surface plateau extending over at least a central portion of the superstrate. A generally planar antenna element is accommodated by and mounted between the substrate and the superstrate, wherein at least a portion of the transitional periphery of the outer surface of the superstrate has a generally smooth transition from the base to the surface plateau.

The sensor may further comprise a housing supporting the at least two sensor elements. The housing may comprise a resilient material such as polyurethane and can be shaped with the sensing elements positioned within the housing to permit visual observation and palpation of body tissue interposed between the at least two sensor elements. In one embodiment, the housing is shaped like a bowtie having two expanded portions interconnected by a portion more narrow than the expanded portions, each of the two expanded portions having at least one sensor element housed therein. The housing having first and second elongated portions may be interconnected by a third elongated portion, each of the first and second elongated portions having at least one sensor element housed therein. The third elongated portion can be positioned at one end of the two elongated portions so that the sensor housing is generally U-shaped to permit visual observation and palpation of body tissue interposed within the open end of the U-shaped housing.

The portion of the transitional periphery of at least one of the at least two sensor elements can be positioned to provide directional transmission and/or receipt of electromagnetic wave energy. The portions of the transitional periphery of at least two of the at least two sensor elements can be positioned to be directed toward one another. The sensor can comprise at least four sensor elements which define at least two electromagnetic wave transmitters and at least two of the sensor elements define at least two electromagnetic wave receiver elements, with the at least two electromagnetic wave transmitters being positioned opposite the at least two electromagnetic wave receivers. To improve coupling, the portions of the transitional periphery of the at least two electromagnetic wave transmitters can be positioned toward the at least two electromagnetic wave receivers and the portions of the transitional periphery of the at least two electromagnetic wave receivers can be positioned toward the at least two electromagnetic wave transmitters. The at least two electromagnetic wave transmitters can be separated from the at least two electromagnetic wave receivers by body tissue to be monitored by electromagnetic waves. The planar antenna elements of the at least two sensor elements can be square and, for circular polarized of the electromagnetic waves, can be electrically contacted adjacent inner corners of the elements.

In accordance with yet another aspect of the present invention, a sensor comprises at least two sensor elements with each sensor element comprising a first substrate and a second substrate. A generally planar antenna element is accommodated by and mounted between the first substrate and the second substrate of each sensor element and the antenna elements are structured to emit electromagnetic waves from an edge of the antennae and the at least two sensors are angularly oriented relative to and directed toward each other. The angular orientation of the at least two sensors can be approximately 120° relative to each other. Since a variety of angles can be used, including different angles for each sensor element, the angular orientation of the at least two sensors can be adjustable relative to each other.

In accordance with still another aspect of the present invention, a method for evaluating a measurement signal against a reference signal comprises converting a reference signal having magnitude and phase to a complex form and plotting the complex form reference signal in a complex plane to form a reference point. A measurement signal is converted into a complex form and also plotted in the complex plane to form a measurement point. The complex distance between the reference point and the measurement point is determined and the complex distance is compared to a threshold. The method may further comprise the step of generating the reference signal by taking a reference or baseline measurement.

In accordance with an additional aspect of the present invention, a method for evaluating measurement signals against reference signals comprises taking measurements at a plurality of frequencies to generate a plurality of reference signals and converting the plurality of reference signals having magnitude and phase to a complex form. The complex form reference signals are plotted in a complex plane to form a plurality of reference points. Measurements are taken at the plurality of frequencies to generate a plurality of measurement signals which are also converted into a complex form. The complex form measurement signals are plotted in the complex plane to form a plurality of measurement points. A plurality of complex distances between the reference points and corresponding ones of the measurement points are determined and compared to a corresponding plurality of thresholds. This method may further comprise normalizing the reference signals by multiplying all reference signals by a normalization factor so that the maximum reference signal becomes one, and multiplying all measurement signals by the normalization factor. The plurality of thresholds may vary as a function of frequency and, to boost performance, vary such that lower threshold values are used at frequencies where sensor performance is higher.

In accordance with another additional aspect of the present invention, a method for evaluating measurement signals against reference signals comprises taking measurements at a plurality of frequencies to generate a plurality of reference signals and converting the plurality of reference signals having magnitude and phase to a complex form. The complex form reference signals are plotted in a complex plane to form a plurality of reference points. Measurements are taken at the plurality of frequencies to generate a plurality of measurement signals that are converted into a complex form and also plotted in the complex plane to form a plurality of measurement points. A plurality of complex distances between the reference points and corresponding ones of the measurement points are determined and a threshold based on the plurality of reference points is determined. A complex distance curve is determined based on the plurality of complex distances and the area under the complex distance curve is compared to the threshold.

In accordance with still yet another aspect of the present invention, a sensor comprises at least two sensor elements with each sensor element comprising a substrate and a superstrate mounted to the substrate and having a base facing the substrate and an outer surface extending away from the substrate. A generally planar antenna element is accommodated by and mounted between the substrate and the superstrate. A housing supports the at least two sensor elements to maintain a predetermined distance between the two sensor elements. The housing may comprise a resilient material such as polyurethane and may be shaped, and the sensing elements positioned within the housing, to permit visual observation and palpation of body tissue interposed between the at least two sensor elements.

In one embodiment, the housing is shaped like a bowtie having two expanded portions interconnected by a portion more narrow than the expanded portions, each of the two expanded portions having at least one sensor element housed therein. In another embodiment, the housing may have first and second elongated portions interconnected by a third elongated portion, with each of the first and second elongated portions having at least one sensor element housed therein. When the third elongated portion is positioned at one end of the two elongated portions, the sensor housing is generally U-shaped to permit visual observation and palpation of body tissue interposed within the open end of the U-shaped housing. The sensor may comprise at least four sensor elements with at least two of the sensor elements defining at least two electromagnetic wave transmitters and at least two of the sensor elements defining at least two electromagnetic wave receiver elements with the at least two electromagnetic wave transmitters being positioned opposite the at least two electromagnetic wave receivers. The at least two electromagnetic wave transmitters can be separated from the at least two electromagnetic wave receivers by body tissue to be monitored by electromagnetic waves and the planar antenna elements of the at least two sensor elements can be square and be electrically contacted adjacent inner corners of the elements to induce circular polarization of the electromagnetic waves.

In accordance with yet another additional aspect of the present invention, a sensor element for injecting and/or receiving electromagnetic waves into body tissue comprises a housing having a substrate mounted therein. A superstrate is mounted to the substrate and has a base facing the substrate and an outer surface facing away from the substrate. A generally planar antenna element is accommodated by and mounted between the substrate and the superstrate with the housing extending to the outer surface of the superstrate and an electrical shield provided to surround the sensor element except for the outer surface of the superstrate. In one embodiment, the housing is flush with the outer surface of the substrate. In another embodiment, the housing is recessed below the outer surface of the superstrate and defines a transitional periphery interconnecting the housing to the outer surface of the superstrate, wherein at least a portion of the transitional periphery has a generally smooth transition from the base to the surface plateau.

The present invention and its attendant advantages will be further understood by reference to the following detailed description and the accompanying drawings.

BRIEF DESCRIPTION OF THE DRAWINGS

FIG. 1 illustrates a detection system in which the sensors and sensor elements of the invention of the present application can be used.

FIG. 2 illustrates the detection system of FIG. 1 in use to detect extravasation.

FIG. 4B illustrates a side view of use of an antenna array as illustrated in FIG. 4A to pass electromagnetic energy across a surface to detect a change in, for example, the geometry, shape or morphology of the surface corresponding to a change in fluid level or material presence in underlying tissue.

FIG. 4C illustrates a side view of an antenna used to transmit electromagnetic energy to and measure reflected electromagnetic energy from a surface to detect a change in, for example, the geometry, shape or morphology of the surface corresponding to a change in fluid level in underlying tissue.

FIG. 9A illustrates a bottom view of a U-shaped sensor of the present invention including two antenna as illustrated in FIGS. 7A and 7B.

FIG. 9B illustrates a bottom view of a U-shaped sensor of the present invention including two linear arrays of four antennae as illustrated in FIGS. 7A and 7B.

FIG. 19A illustrates "complex distance" as a function of injected volume and frequency in the upper graph and maximum "complex distance" over all frequencies as chicken phantom.

FIG. 19B illustrates "complex distance" as a function of injected volume and frequency in the upper graph and maximum "complex distance" over all frequencies as a function of injected volume in a lower graph for another extravasation study on a double-skinned chicken phantom.

FIG. 19C illustrates "complex distance" as a function of injected volume and frequency in the upper graph and maximum "complex distance" over all frequencies as a function of injected volume in a lower graph for an extravasation study on a single-skinned chicken phantom.

DETAILED DESCRIPTION OF THE INVENTION

Figure 3:
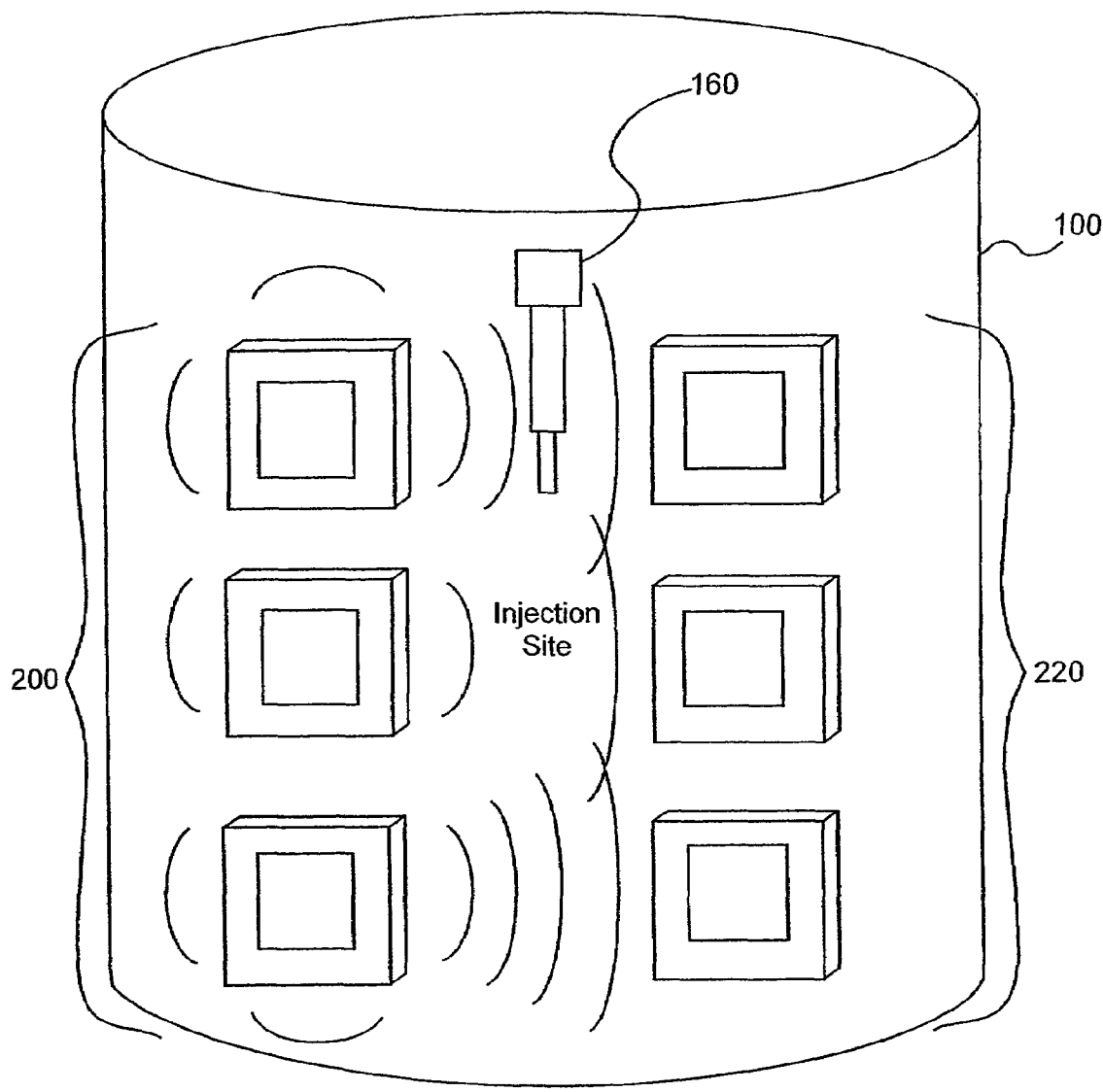
FIG. 3 illustrates a first antenna array positioned about an injection site for use in the detection of extravasation.

While the sensors and methods of the present invention are generally applicable to the sensing of bodily or injected fluid levels or other foreign materials of the levels of such foreign materials in tissues, they will be described herein primarily with reference to extravasation for which it is particularly applicable and initially being utilized. Complex permittivity and permeability govern how an electromagnetic wave will propagate through a substance. Complex permittivity typically has the greatest effect since it varies significantly between tissue types and fluids of interest. The complex permeability of various tissues and many fluids of interest is approximately that of a vacuum, reducing the effect of this parameter. However, some fluids such as MRI contrast agents may have an appreciable complex permeability difference from tissue. Although blood contains small amounts of iron, the permeability value for any significant volume of blood is typically insignificant. Complex permittivity is generally expressed as $$\epsilon^* = \epsilon' - j\epsilon''$$

wherein $\epsilon'$ is the real component of the complex value and is known as the dielectric constant or sometimes simply referred to as the "permittivity." The term $\epsilon''$ is the imaginary component of the complex value and is often referred to as the "loss factor." The ratio of $(\epsilon''/\epsilon')$ is known as the "loss tangent." The complex permittivity (and sometimes permeability) of certain substances differ from the body tissue at certain frequencies. Such differences in permittivity and/or permeability are used for the detection and level monitoring of certain fluids and substances in biological tissue.

The studies leading to the present invention have shown that electromagnetic energy having, for example, a frequency in the range of approximately 300 MHz to approximately 30 GHz (and, more preferably, in the range of approximately 1 GHz to approximately 10 GHz, and, even more preferably, in the range of approximately 3 GHz to approximately 5 GHz) provides good penetration into tissue. In general, such electromagnetic energy is launched into the subcutaneous tissue and a resultant signal is measured. Electromagnetic energy in the frequency range set forth above has been found to transmit through the skin and to transmit or propagate well within, for example, fat. Good transmission through the fat layer is beneficial for detection of extravasation as many extravasations occur in the fat layer. The sensitivity to extravasation of the systems and methods utilizing the present invention is thus increased as compared, for example, to impedance plethysmography wherein the majority of the electrical current passes through highly conductive layers such as skin and muscle where extravasation is much less likely to occur.

Using the detection system configuration illustrated in FIG. 1, the presence or level of a foreign material, liquid, body fluid, or substance in the subcutaneous tissue can be determined. One or more electromagnetic sources 10, typically antennae, transmit electromagnetic waves into the tissue in an area of interest, for example, a portion of an arm 100 of a human patient as shown in FIG. 1. The scattered and/or reflected electromagnetic waves are then received by the launching antenna(e), represented by the dashed line in FIG. 1, and/or by one or more receiving antenna(e) 20. A signal can be transmitted and received with a single antenna which acts as both the source and the sensing element. However, using multiple receiving antennae can be advantageous as noise, motion artifacts, and other anomalies can sometimes be more readily discerned from changes due to abnormal levels of fluid/substance of interest.

A signal is supplied to the active antenna(e) 10 from one or more signal sources 30. The signal source(s) 30 is preferably in communicative control with a data processing and the control unit 40, for example, a computer. The control unit 40 can be in communication with a user interface 50, for example, a keyboard, a monitor etc., and an alarm 60. The data processing and control unit 40 is also preferably in communication with a signal processor 70 which receives signals from the antenna 10 and/or the antenna 20.

In general, the detection system illustrated in the present application is well suited for the detection of abnormal and/or changing levels of a variety of fluids in the human body, including both body fluid and foreign substances. In several embodiments of the detection system, one or more antennae as described above can be used to determine if an extravasation has occurred during an injection procedure. Several antenna(e) designs, configurations and/or placements are described below in the context of detection or determination of extravasation.

For example, FIG. 2 illustrates the use of the detection system of FIG. 1 in the detection of an extravasation 120 during an injection procedure. The transmitting antenna 10 and the receiving antenna 20 are positioned on opposing sides of an injection site wherein a catheter 160 is positioned within, for example, a vein 110. The catheter 160 can, for example, be in operative connection with a source of pressurized injection fluid such as a syringe 170 in connection with a powered injector 180 as known in the art.

The detection system uses electromagnetic waves in the RF and microwave region, well below the optical frequency range. Applicators/antennae to transmit and/or receive electromagnetic energy for use in the present invention are, for example, resonant structures and may take on several forms including, but not limited to, the following: microstrip antenna(e), waveguide(s), horn(s); helical antenna(e) and dipole antenna(e) as known in the art. As used herein, the term "microstrip antenna" refers generally to a thin, low-profile antenna of a wide variety of patterns including, but not limited to, linear, square, circular, annular ring, triangular, rectangular, dipole, tapered slot, planar spiral and others.

In the RF and microwave frequency electromagnetic energy ranges of detection system, resonant structures or other energy transmitting antennae interact with the tissue of interest via nearfield interactions and propagated waves. Energy is exchanged with the tissue in the nearfield and waves are propagated into the tissue. Reflections and scattering occurs at boundaries when permittivity and/or permeability variations and differences occur.

In the detection system, a measured signal is compared to a reference signal or signals to determine if an abnormal (for example, elevated) level of fluid is present in the area of tissue being monitored. A reference signal can, for example, be a baseline signal that is measured when the fluid/substance level of interest is known or in a known state. Following the baseline determination, a search mode is entered where changes in reflected or scattered waves are detected by measuring the received signal(s) and comparing them to the reference signal(s). If, for example, the measured signal deviates from the reference signal by a predetermined amount or in a predetermined manner, the alarm 60 can be activated. In an injection procedure, the injection can be stopped upon activation of the alarm 60. For example, the control unit 40 can be in communication with the powered injector 180 to stop an injection procedure upon detection of extravasation.

Measurements and signal processing can be made in the time domain and/or the frequency domain as known in the art. In the frequency domain, the signal source is generally a sinusoidal wave source in which the frequency is swept or stepped through a desired frequency range. At each frequency of interest, the magnitude and/or phase of the measured signal can be compared to the magnitude and/or phase of the reference signal to detect changes of, for example, a pre-determined amount. Alternatively, in the time domain, the signal source can be a substantially narrow impulse or sharp step that excites the resonant modes of the sending antenna(e) which in turn launch electromagnetic waves into the tissue of interest. Fluid or substance presence or level changes alter the received signal(s) such that they differ from the reference signal in terms of delay, frequency content, and/or overall shape.

The detection system also embodies other types of measurements and signal processing. When using the same antenna(e) to send and receive energy, such measurement modes can include, for example, antenna impedance or resonant mode frequency shift detection. Furthermore, more sophisticated signal processing techniques of the reference and/or received signals can be employed. For example, the signals may be mathematically manipulated, such as averaged, integrated, median filtered, band pass filtered, low pass filtered, or high pass filtered in the time or frequency domain to emphasize subtle patterns in the data that may not be as readily apparent when simple reference subtraction/comparison is performed.

In general, to compare or to make a comparison refers to making a decision or judgment based upon a relationship between two or more measurements, sets of measurements, or functions of measurements. The relationship is generally expressed as a mathematical relationship, algorithm or heuristic. For example, a comparison of magnitude or "complex distance" from a reference or baseline measurement, as further described below, can be made. It is also possible to compare the slopes or rate of change of the received and reference signals. An algorithm similar to that applied in statistical process control can, for example, be applied whereby an abnormality is judged to occur if more than a predetermined number of successive measurements, for example four successive measurements, are on one side of the reference signal, or if one measurement is outside of a standard band, or if there is a trend of a predetermined number of measurements, for example seven measurements, moving in a consistent direction. As known to those skilled in the art there, are many other comparisons that can be made.

In a first antenna array positioned about an injection site illustrated in FIG. 3, two generally linear arrays of antennae are used. In this embodiment, one array of antennae is an active, launching/transmitting, array 200 and an opposing array of antennae on the other side of the injection site is a passive, receiving, array 220. The signal source of the system excites or drives the active array 200 via, for example, amplifiers by using sinusoidal or impulse waveforms. The signal source(s) create an electromagnetic wave which is launched generally normally (perpendicularly) to the skin surface and into the subcutaneous tissue. The wave then scatters and propagates through the subcutaneous tissue (for example, through adipose/fat tissue). Tissue layers that are more conductive than fat, such as muscle and skin, tend to reflect and guide the electromagnetic energy. The antennae of the passive antennae array 220 then receive the signals which are, in turn, processed by the signal and data processing subsystems. The received or measured signals are then compared to the reference, for example baseline, signals that were collected during the baseline procedure. As discussed above, baseline measurements can be repeated or updated to create a running baseline. As known by those skilled in the art, a wide variety of microstrip antenna designs are suitable for use in the present invention including: line, square, circular, annular ring, triangular, rectangular, dipole, tapered slot, planar spiral and others. In general, any design that yields sufficient energy coupling in the preferred frequency ranges set forth above are suitable for use in detection system.

Figure 4A:
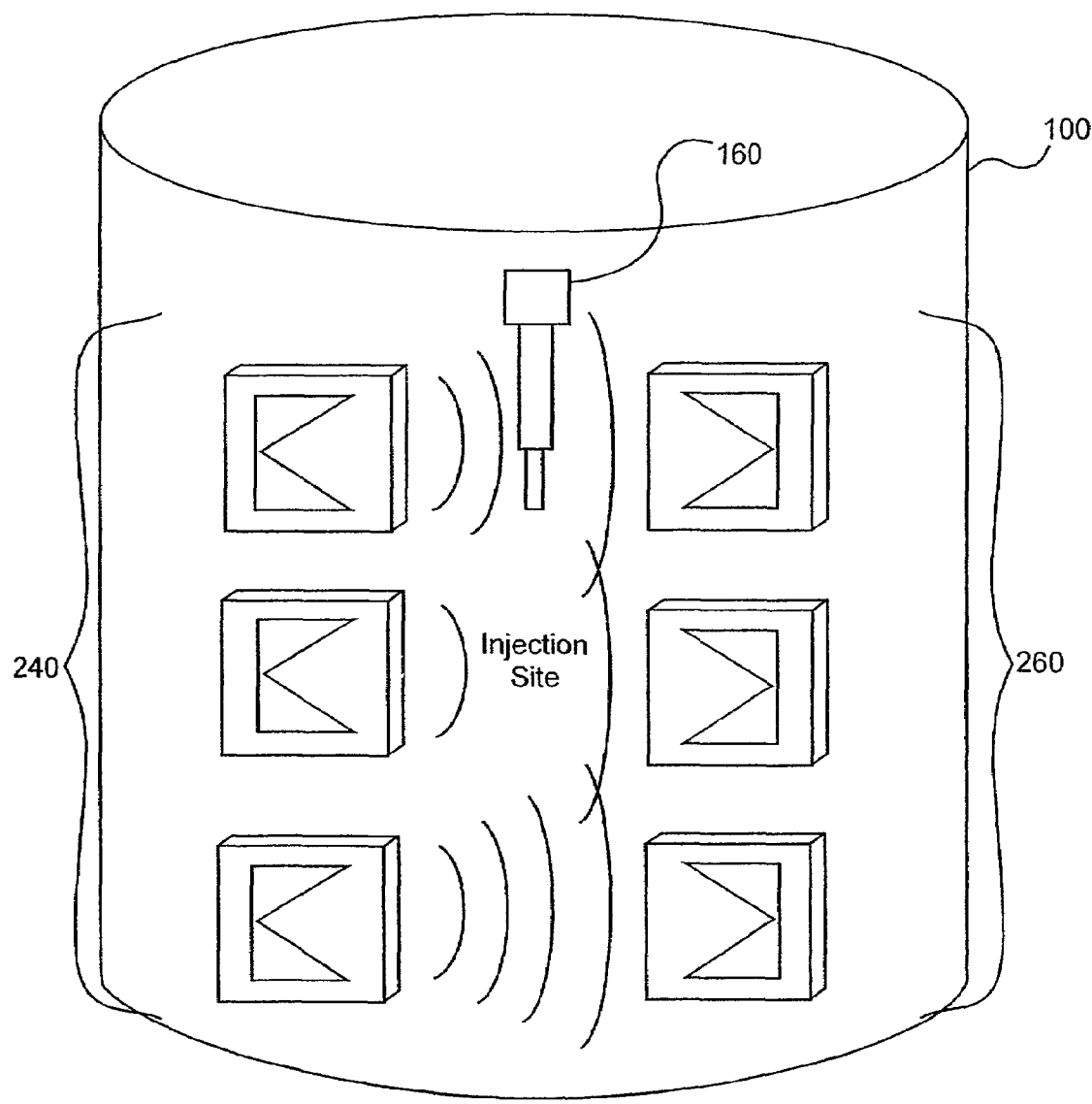
FIG. 4A illustrates a second embodiment of an antenna array including tapered-slot antennae.

In FIG. 4A, a generally linear array 240 of transmitting microstrip antennae with a tapered-slot design are illustrated. The tapered-slot design yields improved directionality and increased bandwidth. The antennae or array 240 are angled toward the skin of arm 100 so that the waves can be launched into the tissue, yet in the general direction toward a passive/receiving antennae 260. Use of such tapered-slot antennae can improve signal coupling and overall sensitivity.

In another embodiment of the detection system, electromagnetic waves are propagated in the vicinity of the surface of the skin or other body surface using antennae, for example arrays of antennae as illustrated in FIG. 4A, above or close to the surface. The propagated waves interact with the surface in a manner that is affected by the surface shape, geometry or morphology. This method can be useful, for example, when the tissue of interest has a thin fat layer. In this embodiment of the present invention, surface/skin deformation caused by the fluid/substance of interest can be detected by monitoring signals reflected and/or scattered by the surface. Tapered-slot antennae in a configuration similar to that shown in FIG. 4A can, for example, be used to propagate surface waves across moderately conductive skin. For example, FIG. 4B illustrates transmission of electromagnetic waves across the surface of the arm 100 by a pair of transmitting/receiving antennae 250a and 250b. Surface deformation caused by changed, elevated or abnormal fluid levels (for example, extravasation) induce a change in the signal measured by the antenna(e) 250a and 250b. FIG. 4C illustrates another embodiment in which a transmitting/receiving antenna 260 transmits electromagnetic energy generally normal to the surface of the arm 100 and receives a reflected signal. Once again, surface deformation induces a change in the measured signal. In the embodiment of FIG. 4C, separate transmitting and receiving antennae can be used as described above as either a single antenna pair or as an array of multiple transmitting/receiving antennae.

Figure 5:
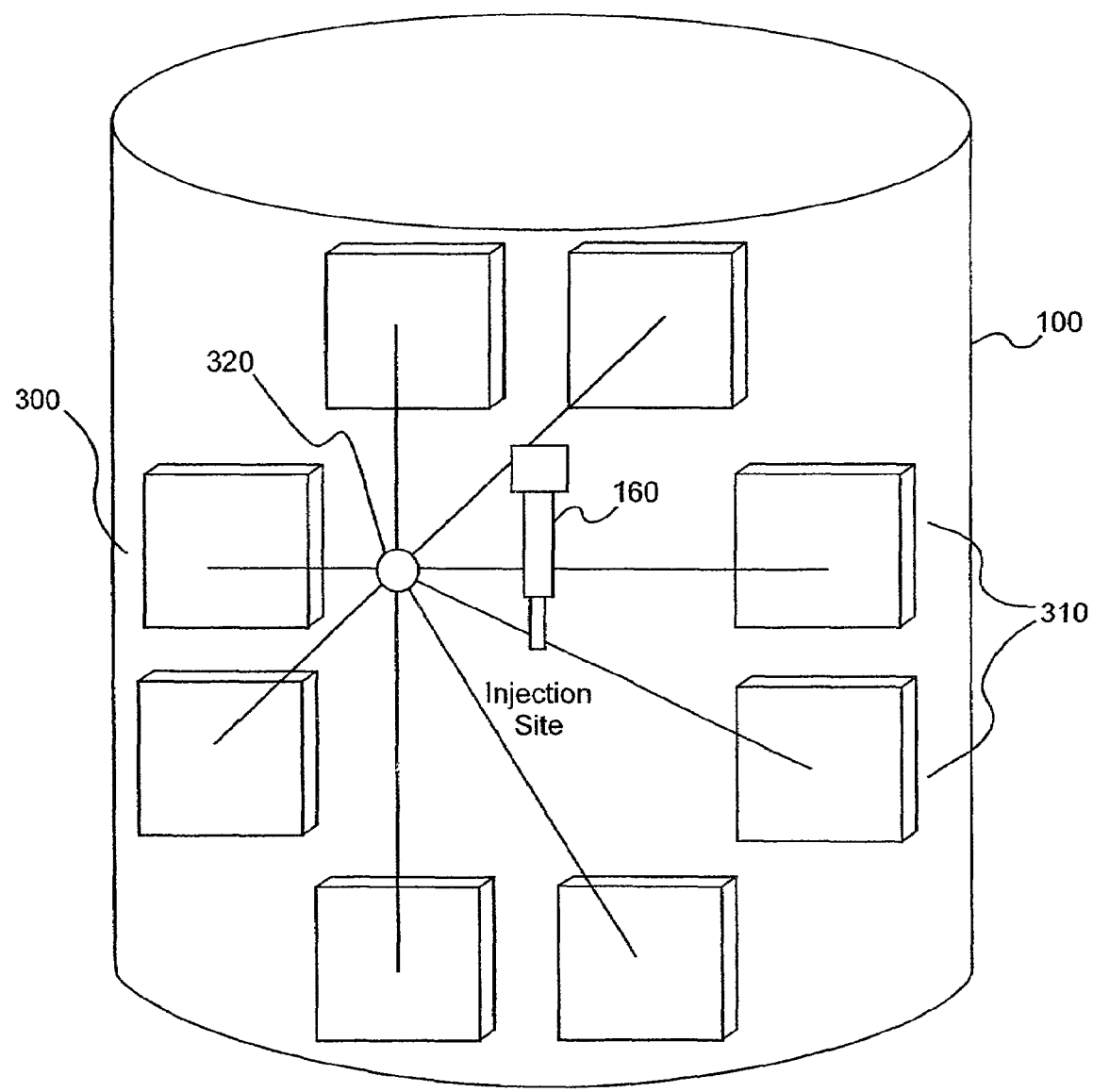
FIG. 5 illustrates a second antenna array positioned about an injection site for use in the detection of extravasation.

Another embodiment of a multiple antenna configuration or antenna array is shown in FIG. 5 wherein a plurality of individual antennae 310 are arranged to surround the area to be monitored. The web array of antennae 310 in FIG. 5 enables a phasing approach to concentrate the wave energy at a particular location 320. The phased drive signals to each antenna can then be altered such that the focal point 320 is moved in a scanning pattern. This phasing approach can increase the overall sensitivity of the system. Furthermore, directional couplers can be employed, as known in the art, to allow the transmitting antennae in the web array to also perform as receiving antennae simultaneously. Directional couplers are used in equipment such as network analyzers to allow the analyzer to send energy to a device, like an antenna, while simultaneously receiving reflected energy from the device/antenna. Therefore you can transmit and receive on an antenna simultaneously.

The detection system illustrated in the present application is not limited to the antenna configurations or arrays set forth above. A wide variety of antenna configurations are suitable for use in the present invention. In general, any antenna configuration positioned near the anticipated location of the liquid or substance to be detected or monitored is suitable.

For example, extravasation typically occurs in the immediate vicinity of the injection site, near the position of the catheter tip. Extravasation may sometimes occur, however, at a site remote from the injection site. In the detection system of the present application, extravasation can be detected at the injection site and at site(s) remote from an injection site (generally along a path of potential extravasation) using, for example, antennae positioned as an array along a path of potential extravasation.

Figure 6:
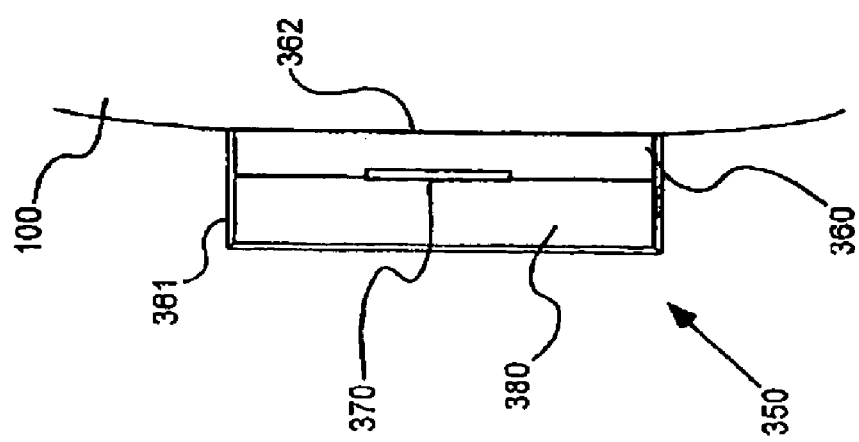
FIG. 6 illustrates an embodiment of a transmitter and/or receiver including a coupling or superstrate layer suitable for coupling the transmitter/receiver to the skin.

Because certain body surfaces such as skin are somewhat reflective to electromagnetic waves in the frequency ranges used in the present invention, coupling the waves into the surface and tissue can improve system performance. Coupling can, for example, be improved by providing a layer of material in contact with the skin/other surface of interest (for example, the surface of an internal organ) that couples with the surface by having an intrinsic impedance similar to the surface. Such material may comprise, for example a relatively high permittivity, low-loss material, such as magnesium calcium titanium dioxide, $MgCaTiO_2$. A disposable de-ionized water pouch can also be used. Preferably, deformation of such a water pouch or container during use thereof is limited as deformation can impact the received or measured signal. In that regard, a thin-walled, rigid water container can be used or a pressurized water pouch that limits deformation can be used. FIG. 6 illustrates a sensor 350 in accordance with the present invention wherein an intermediate, spacing or superstrate layer 360 of a coupling material as described above is in direct contact with the skin of the arm 100, while an antenna, for example, a resonant structure 370, is spaced from the skin by the intermediate or superstrate layer 360. In the embodiment of FIG. 6, resonant structure 370 is positioned within a substrate 380 and the sensor is shielded up to the transmitting/receiving face 362 of the sensor. A microstrip antenna 350' used in several studies that led to the invention of the present application was structured substantially the same as the sensor 350 but without the shielding.

Figure 7E:
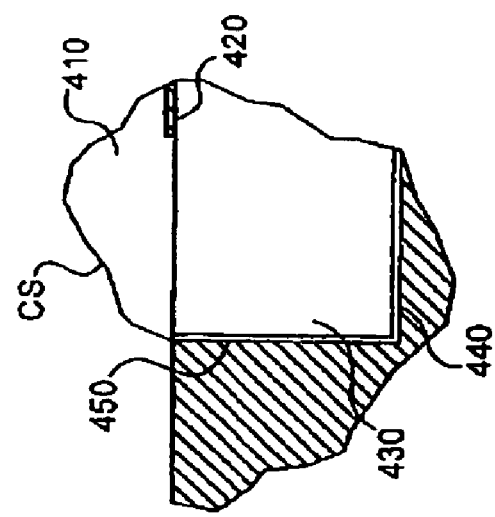
FIG. 7E is a broken-away, side, cross-sectional view of an alternate embodiment of an antenna of the present invention showing a curvilinear tapered superstrate.
Figure 7D:
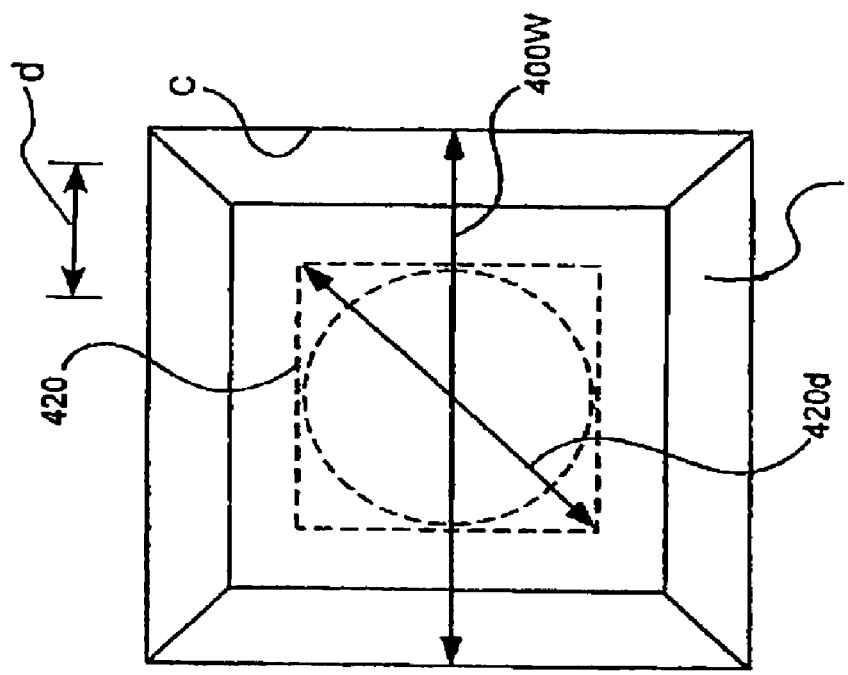
FIG. 7D is a plan view of the antenna or FIG. 7A showing resonance sizing of a square patch antenna and a circular patch antenna, one of many alternate patch antenna geometries.
Figure 7A:
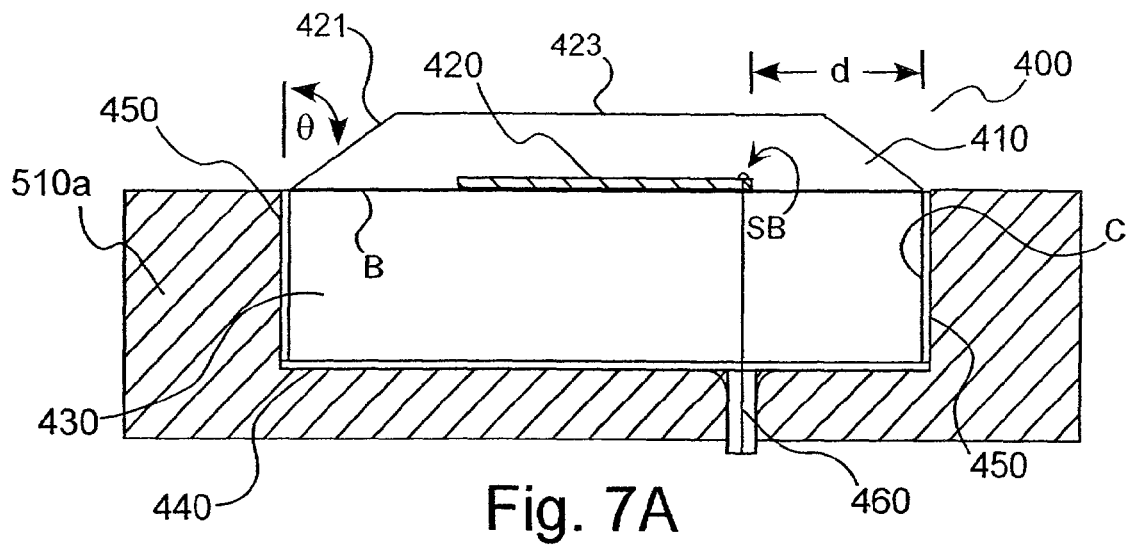
FIG. 7A illustrates a side, cross-sectional view of an embodiment of an antenna including a sensor element of the present invention with a linearly tapered superstrate.
Figure 7B:
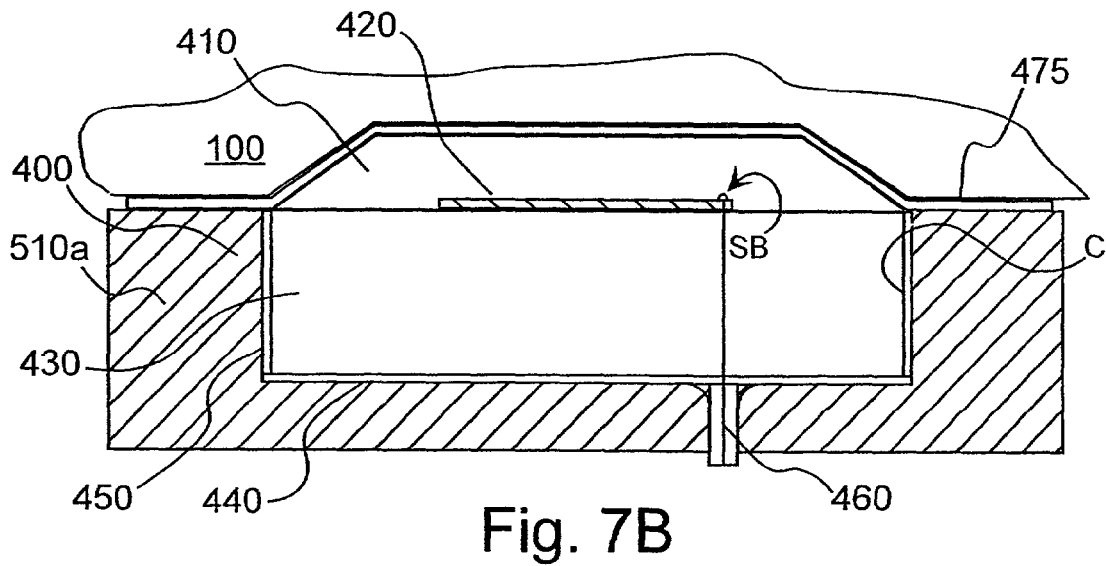
FIG. 7B illustrates a side, cross-sectional view of the antenna of FIG. 7A coupled to a patient's arm.

FIGS. 7A and 7B illustrate an embodiment of a microstrip antenna 400 in accordance with the present invention. Like the antenna 350, the antenna 400 includes a superstrate layer 410 fabricated from a coupling material and having an outer surface extending away from the substrate 430 which contacts the skin of the arm 100, see FIG. 7B. An antenna or resonant structure 420 is positioned on a substrate 430. In general, the antennae or resonant structures of the present invention are fabricated from a conductive material such as copper, silver, gold or other appropriate material as known in the art.

Preferably, the substrate material is a moderate to high permittivity, low-loss material, such as $MgCaTiO_2$, and is often the same as the superstrate to prevent discontinuities between the substrate and the superstrate. However, prototypes with differing materials for the superstrate layer and substrate layer have been fabricated and successfully operated. In general, any material with moderate to high permittivity values (for example, in the range of approximately 10 to approximately 100 and, more preferably, in the range of approximately 50 to approximately 80) and low-loss characteristics such that its intrinsic impedance is reasonably close to the surface of the tissue to be interrogated will be suitable. Furthermore, materials with low moisture absorption characteristics and low permittivity to temperature correlation are also desirable.

In some of the microstrip antennae used in the studies leading to the present invention, the antennae were fabricated from a ceramic laminate material coated with thin layers of copper on the front and back thereof. In particular, a product sold under the name RT/duroid® 6010LM by Rogers Corporation of Chandler, Ariz., was used. Such microwave laminates are ceramic-PTFE (polytetrafluoroethylene) composites designed for electronic and microwave circuit applications requiring a relatively high dielectric constant or permittivity. RT/duroid 6010LM laminate has a dielectric constant of 10.2±0.25. The laminates used to fabricate the microstrip antennae were approximately 2.5 mm thick for the substrate and 1.25 mm for the superstrate and were supplied with both sides thereof clad with ½ oz./ft² electrodeposited copper foil (cladding thickness of approximately 16 µm -¼ to 2 oz./ft² electrodeposited copper foil available with cladding thicknesses of 8 µm to 70 µm).

In fabricating the sensor elements/sensors of the present invention, some of the copper material was etched from the top of the laminate to form a generally planar microstrip antenna element or resonant structure 420, thereby forming a margin between the outer edge of the resonant structure 420 and the outer edge of the substrate 430. In that regard, a margin d (see FIG. 7A) was created between the resonant structure 420 and the periphery of the substrate 430. The copper on the bottom side of the laminate forms a ground plane 440 for the antenna 400. Side shielding 450 of a conductive material can be provided to, for example, improve tissue coupling and reduce the leakage of stray energy. In certain embodiments, stray surface waves can, for example, increase motion and other artifacts. However, such "stray" or side energy can also be used to monitor surface geometry changes as discussed above in connection with FIGS. 4A through 4C. Silver side shielding was used in several antennae of studies leading to the present invention.

Side shielding 450 and ground plane 440 form an electrically conductive cavity C. Preferably, the resonant structure 420 and the cavity C resonate together in the frequency range of interest. Such resonance improves efficiency by increasing power output relative to power input for transmission, and power received relative to power available for reception for receipt. In general, margin size impacts resonance of a patch or resonant structure with a cavity. It was found by the present inventor that when the diagonal dimension 420d (see FIG. 7D) of a square resonant structure 420 is generally equal to the non-diagonal distance or side width 400w across the cavity C (total antenna width), resonant structure 42 and the cavity C resonate together in the frequency range of interest. It is believed that the first mode of the resonant structure or patch 420 resonates with the second resonant mode of the cavity C. In this embodiment, the matching of the diagonal dimension 420d with the non-diagonal distance or side width 400w, determines the size of margin d.

Although square resonant structures 410 were used in the studies resulting in the present invention, it is clear to one skilled in the art that many alternative antenna element or resonant structure geometries, including for example circular or rectangular, can be used in the sensor elements and sensors of the present invention. Circular resonant structures can, for example, provide increase bandwidth as compared to square resonant structures in certain embodiments.

Energy is supplied to the resonant structure 420 via, for example, a microcoaxial cable 460 as known in the art. Energy can be supplied to an inner corner of the resonant structure 420 to induce circular polarization which can improve coupling between antennae by decreasing the sensitivity of such coupling to the relative orientations of the antennae. In the fabrication of the antennae or sensor elements/sensors of the present invention, a base of the superstrate layer 410 was secured to the substrate 430 using an appropriate adhesive, such as a cyanoacrylate or "superglue." In that construction, potential air pockets adjacent the resonant structure 420 are filled with the superglue to substantially avoid any negative effect on transmission of the microwaves. However, an indentation corresponding to and receiving the resonant structure 420 can be formed on the underside of the superstrate layer 410. Such an indentation can also or alternately accommodate a solder bump SB formed by connection of the center conductor of the microcoaxial cable 460.

In some of the microstrip antennae used in the studies leading to the present invention, the antennae superstrate layer was fabricated from a ceramic filled PTFE laminate material reinforced with woven fiberglass available from Rogers Corporation of Chandler, Ariz. under product number RO3210. That material has a dielectric constant of 10.2±0.5. It was discovered that beveling the edges of the superstrate layer 410 to form a transitional periphery 421 interconnecting a base B of the superstrate layer 410 to an outer surface plateau 423 extending over at least a central portion of the superstrate layer 410 improved skin conformance and reduced motion artifacts in a measurement signal resulting from patient movement, see FIG. 7A. As illustrated, for example, in FIGS. 7A and 7B, the outer edges of the superstrate layer 410 are beveled at an angle $\theta$ which is greater than 0° and less than 90°. Preferably, $\theta$ is between approximately 20° and 50°. In several of the antennae or sensor elements/sensors studied in the Experimental Example set forth below, $\theta$ was approximately 30°. In addition to improving skin conformance/coupling, the superstrate layer 410 can have only a portion tapered so that it can also direct energy in the direction of the tapered portion, for example toward a receiving antenna in the manner of a "microwave lens" to improve transmission between antennae. Rather than a linear taper as shown in FIGS. 7, 8 and 9, giving the upper surface of the superstrate layer 410 an appearance of a truncated pyramid, the taper can be a smooth curvilinear surface CS, as shown in FIG. 7E, to improve the conformance of the superstrate 410 to a patient's skin.

Figure 7C:
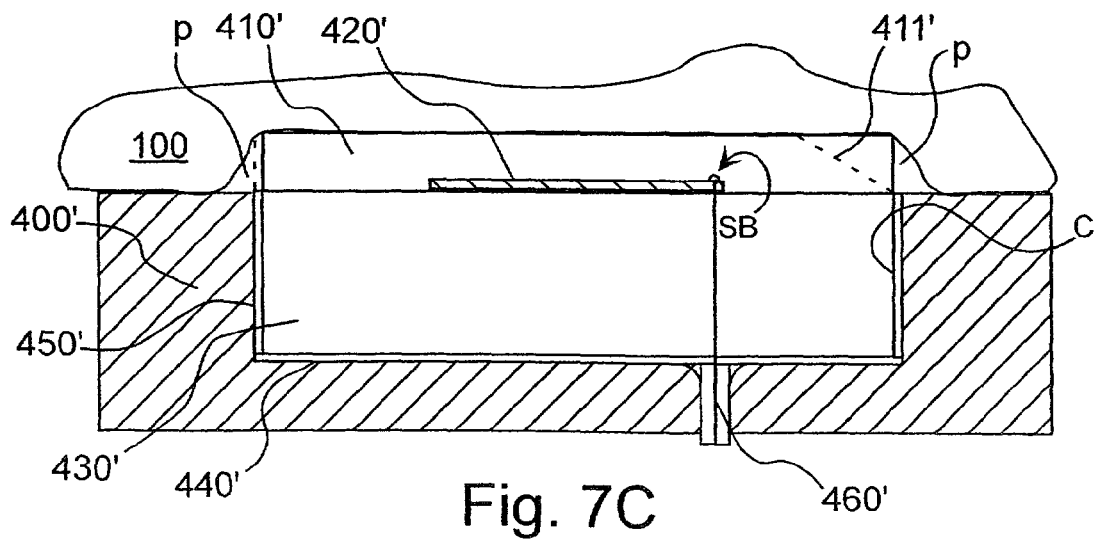
FIG. 7C illustrates a side, cross-sectional view of an antenna of the present application with a square superstrate coupled to a patient's arm.

FIG. 7C illustrates an antenna 400' which is substantially identical to the antenna 400 except that the superstrate 410' of the antenna 400' is square, rather than being beveled or curvilinear. In comparing FIGS. 7B and 7E to 7C, it is seen that the skin tissue of the arm 100 does not conform as well to the contour of the antenna 400' as it does to the contour of the antenna 400, resulting in the formation of air pockets p on the periphery of the antenna 400'. Such air pockets can, for example, scatter the microwave energy, negatively affect coupling and cause increased artifacts as a result of subject patient motion.

Antennae of the sensor elements/sensors of the present invention can be made to have somewhat directional transmission and/or reception of microwaves by having only a portion of the transitional periphery of the outer surface of the superstrate have a generally smooth transition from the base of the superstrate to the surface plateau of the superstrate in the desired directional transmission and/or reception. For example, the antenna 400' as shown in FIG. 7C can be made to be provide directional transmission and/or receipt of microwaves by making only a portion, such as one side of the transitional periphery 411', have a generally smooth transition so that transmission and/or reception is improved in that direction, to the right side of FIG. 7C. For such antenna construction, the shield 450' should be extended as shown by the dotted lines. Thus, one or more pairs of antennae can be mated to favor transmission by one antenna and receipt by its mate.

Whether the sensors of the present invention comprise a single antenna, a pair of antennae or an array of more than two antennae, the injection site preferably remains open or available for visualization and/or palpation. The sensors and methods of the present invention readily afford such availability. As illustrated, for example, in FIGS. 2, 3, 4A and 5, a plurality of antennae can be placed on the subject/patient in a disconnected state. However, it is often desirable to generally maintain a predetermined distance between antennae.

FIGS. 8A through 8D illustrate a sensor 500 including a sensor support, housing or base member 505 that is shaped like a "bowtie" having first and second expanded portions or base sections 510a, 510b interconnected by a more narrow portion or flexible bridge 520. The flexible bridge 520 allows some bending and/or twisting of the first base section 510a and the second base section 510b relative to each other to conform to, for example, a patient's arm or other region of interest. The base sections 510a, 510b each receive or house an antenna 400 with the bridge 520 generally or approximately maintaining a predetermined distance or range of distances between the antennae 400, while providing the needed flexibility to conform to a patient's tissue, see, for example, FIG. 8D, and allowing access to the vicinity of the detection area, for example, an injection site in an extravasation detection.

For a number of applications, the sensor base 505 is thus preferably fabricated from a durable, flexible/resilient material having a relatively low dielectric constant. Many polymeric materials, such as, for example, polyurethane, are suitable for fabrication of the sensor base 505. In several embodiments of the sensor of the present invention, the sensor base 505 was molded from an integral piece of polyurethane. It is also contemplated that the sensor base 505 can be fabricated of more rigid materials for given applications.

Figure 8A:
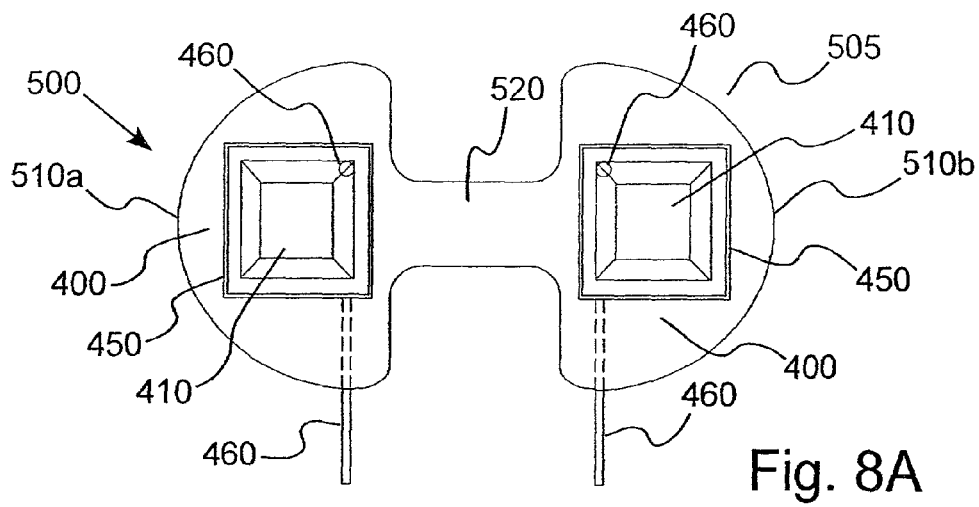
FIG. 8A illustrates a bottom view of a "bowtie" sensor of the present invention including two antenna as illustrated in FIGS. 7A and 7B.
Figure 8B:
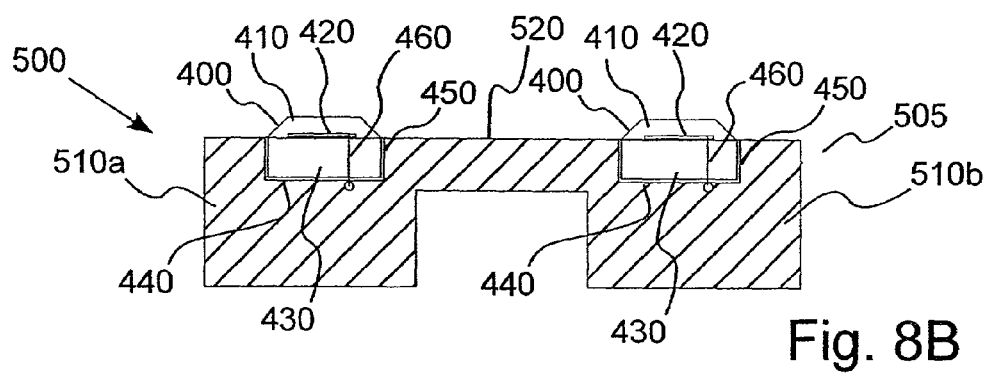
FIG. 8B illustrates a side, cross-sectional view of the sensor of FIG. 8A.
Figure 8C:
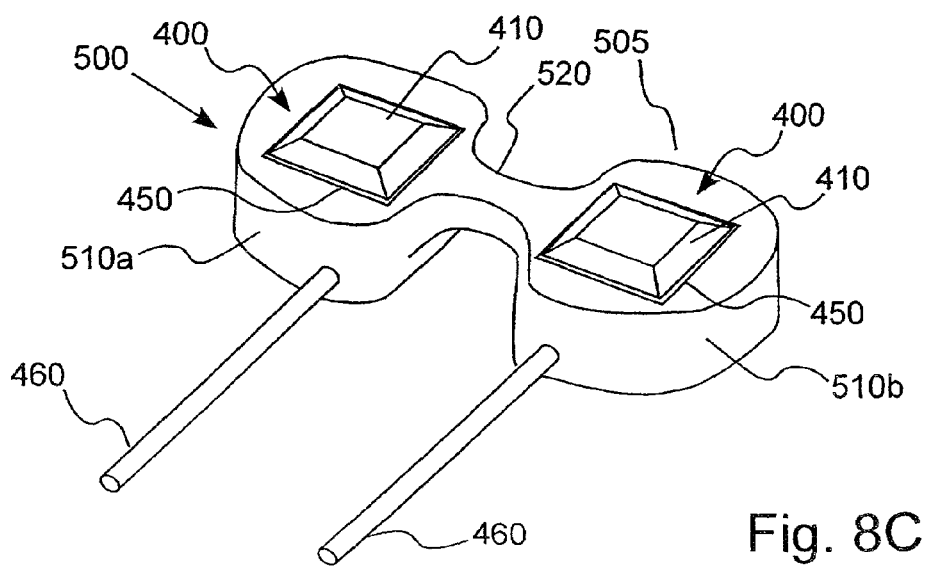
FIG. 8C illustrates a perspective view of the sensor of FIG. 8A.
Figure 8D:
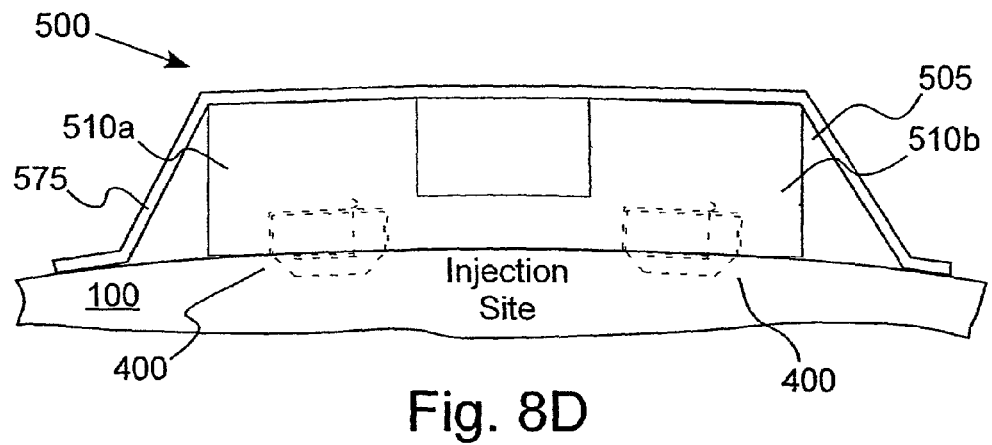
FIG. 8D illustrates a side view of the sensor of FIG. 8A coupled to a patient's arm.
Figure 8E:
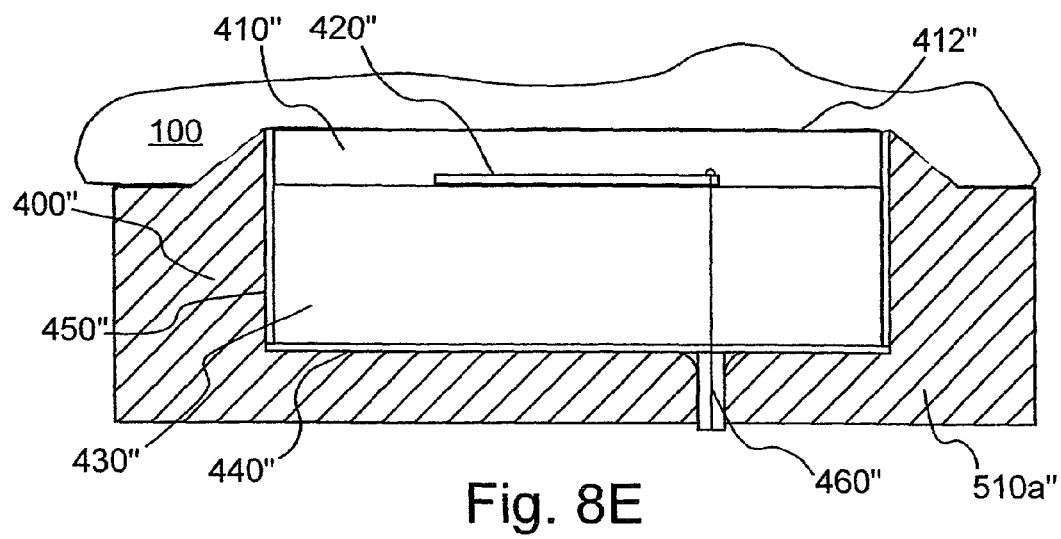
FIG. 8E illustrates a side, cross-sectional view of an embodiment of an antenna of the present invention positioned within a base member having a tapered profile to assist in conforming to tissue.

It is further contemplated that the linear taper or smooth curvilinear surface, described above relative to the superstrate 410, can be formed on the sensor support, housing or base member 510a", see FIG. 8E, rather than on the superstrate 410" to assist in conforming to tissue. The superstrate 410" in such an embodiment can be made generally flat or planar over its outward transmitting/receiving surface 412". If a support, housing or base member defines the taper, linear or curvilinear, or is generally flush with the face of an antenna, such as antenna 400", the shielding 450" for antenna 400" can be extended to the transmitting/receiving face 412" of superstrate 410" as illustrated in FIG. 8E. Also see FIG. 6.

The bridge 520 maintains a separation between the first base section 510a and the second base section 510b and the respective antennae 400 to ensure suitable coupling and to provide visual and tactile access to the injection site as defined, for example, by a catheter tip.

FIGS. 9A and 9B illustrate alternative embodiments of sensors 600, 700 of the present invention that provide flexibility to conform to the patient's tissue and allow access to the vicinity of the detection area, for example, an injection site in an extravasation detection application. The sensor 600 of FIG. 9A is a generally U-shaped sensor including a sensor support, housing or base member 605 having a first base section 610a and a second base section 610b connected by a bridge 620. As described above for the sensor 500, the sensor base 605 is preferably fabricated from a resilient material such as a polyurethane; however, other more rigid materials are contemplated for use in the present invention. Each of the first base section 610*a* and the second base section 610*b* supports an antenna 400 as described above.

The sensor 700 of FIG. 9B is also a U-shaped sensor including a sensor support, housing or base 705 having a first base section 710*a* and a second base section 710*b* connected by a flexible bridge 720. The sensor base 705 is also preferably fabricated from a resilient material such as a polyurethane; however, other flexible materials and more rigid materials can be used. Each of the first base section 710*a* and the second base section 710*b* supports a linear array of antennae 400. While each of the antennae 400 are shown as being the same size, the sizes of the antennae can vary to provide various resonance frequencies of interest for the sensor or to generally increase the bandwidth of the sensor and therefore frequency range over which it is sensitive.

Each of the antennae 400 of the sensor 700 of FIG. 9B can be connected to a power source/measurement device via individual wires or connective paths. Alternatively, integrated power/signal splitters, as known in the art, can be used. In that regard, as known in the RF communications arts, power splitters can be integrated into microstrip (planar) antenna designs, such that an array of antennae located on one layer can be fed through apertures located on another layer which are in turn fed by a power splitter and feeds on a third layer. This structure allows the simultaneous feeding of multiple transmitting antennae with one input signal or connection 730. Such a splitting method is also an effective method of combining signals from multiple receiving antennae into one signal or connection 740 to be processed. Adjustments in phasing for the antennae that make up the transmitting/receiving arrays can be done during the design phase, but will be fixed once the device is fabricated. This method can offer advantages in sensors of the present invention by, for example, improving directionality and therefore signal-to-noise ratio (SNR) for the sensor.

Figure 23:
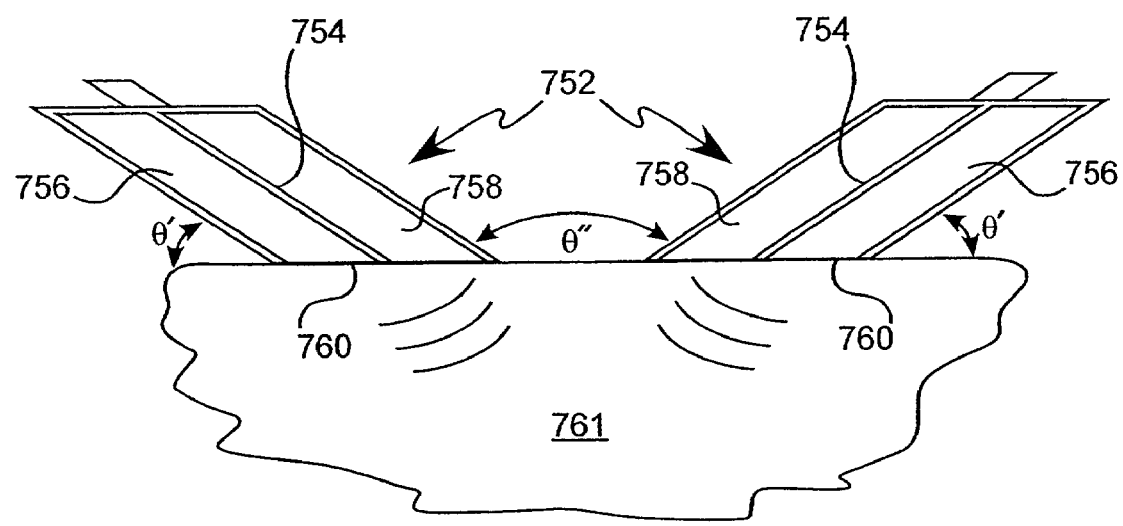
FIGS. 23 and 24 illustrate an alternate embodiment of a sensor with opposing directional planar antennae.
Figure 24:
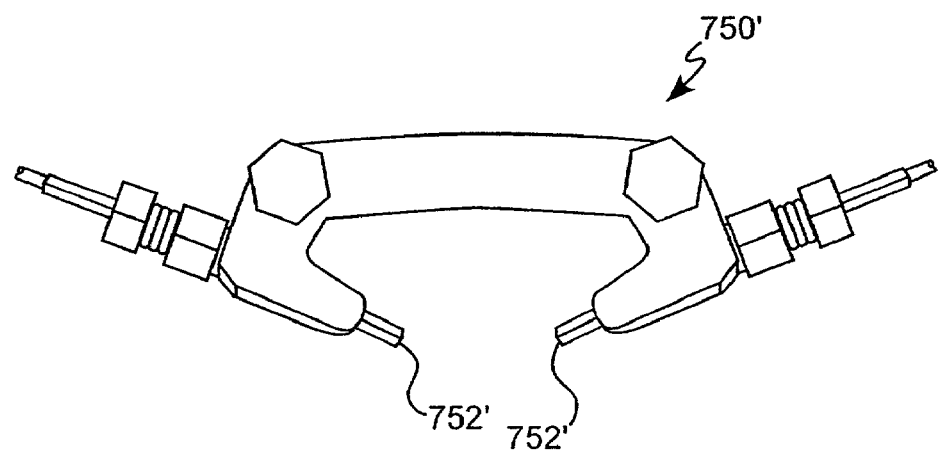

FIG. 23 illustrates another embodiment of a sensor 750 of the present invention with sensor elements comprising opposing directional planar antennae 752. The directional planar antennae are structured similar to the antennae used in the other sensors of the present application with an antenna element 754 mounted between first and second substrates 756, 758 with shielding 759 surrounding the antennae except for the electromagnetic emitting/receiving faces adjacent to tissue 761 being sensed. However, the directional planar antennae 752 are structured to emit microwaves from the ends or edges 760 of the antennae 752 rather than from the planar faces of the antennae. Such antennae, referred to as "edge-firing" types, are well known in the art and include Yagi, Quasi-Yagi, Tapered Slot, Vivaldi and others. FIG. 24 illustrates an experimental mounting arrangement wherein the angular orientations of the antennae 752 relative to each other can be varied. Currently, an angular orientation θ' of approximately 30° to a surface of a body to be sensed, i.e., an angle θ" of approximately 120° relative to each other, is believed to be preferred; however, the specific angular orientations can be any reasonable value required for a given application and it is contemplated that different angular orientations can be used for each of the antennae.

EXPERIMENTAL EXAMPLES

1. Inorganic Phantom Experiments.

Several experiments demonstrating the use of the sensors of the present invention were carried out using single and dual microstrip patch antenna configurations and an inorganic phantom to represent human tissue. Such inorganic phantoms provide the opportunity to accurately control both the position and amount of a simulated extravasation in an environment of generally known and simple dielectric properties as compared to human tissue.

Below approximately 1 GHz, the wavelength becomes too large to provide adequate sensitivity to changes of interest in the tissue and approaching and, beyond 10 GHz, the penetration of the waves into the tissue becomes too small to provide adequate sensing depth. Thus, the antennae of the present invention that were used for this experiment were designed to resonate at an intermediate frequency of approximately 4 Ghz.

The microstrip antennae used in the studies leading to the present invention were designed using Finite Difference Time Domain (FDTD), a well known modeling technique. Standard equations, generally available for well-understood geometries, were used to determine approximate dimensions required for the resonant structures of the various antennae in the studies resulting in the present invention. Following that, substrate thickness was chosen to be a fraction of the wavelength corresponding to the primary resonant mode of the resonant structure. Finally, FDTD simulation techniques were used to refine dimensions and determine the best location for the feed connection. A FDTD software package available from Remcom Inc. of State College, Pa. was used for the design of the antennae which were then etched and fabricated using well known laboratory techniques. As known in the art, moving a feed point outward towards the edge of a square resonant patch will (to, for example, induce circular polarization) increases the impedance of the antenna. Ultimately an impedance similar to the driving circuitry is desired to maximize power transfer.

Figure 11:
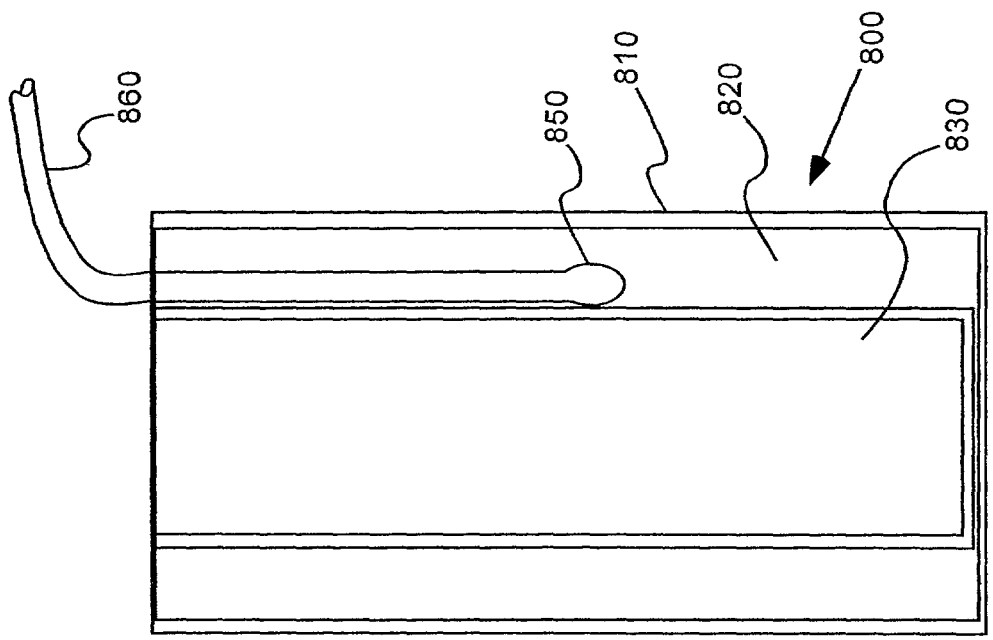
FIG. 11 illustrates a side, cross-sectional view of the phantom of FIG. 7.
Figure 10:
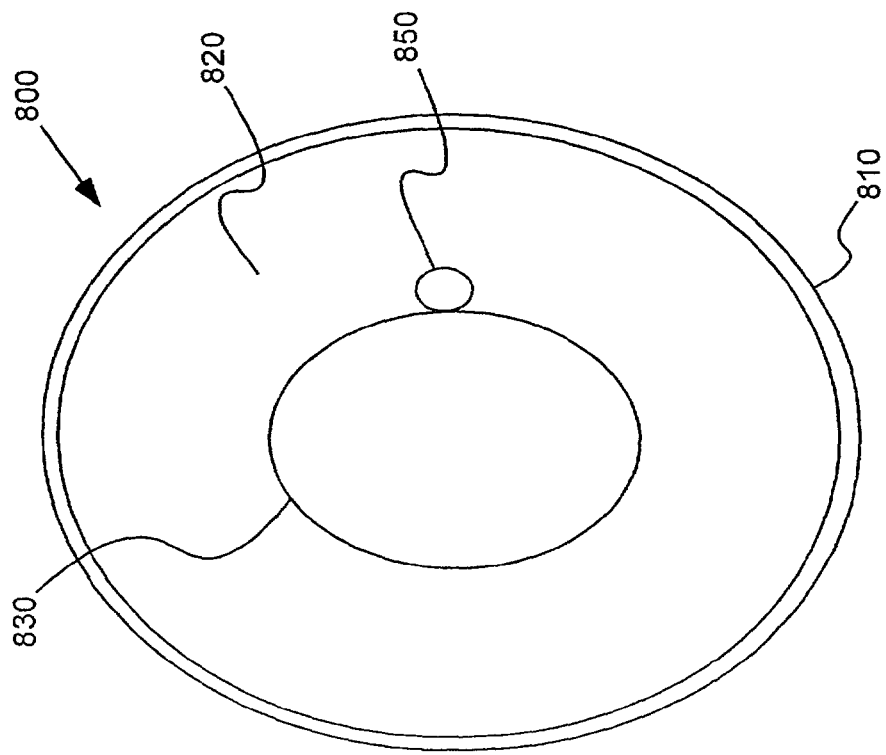
FIG. 10 illustrates a top view of an embodiment of a phantom used to model elevated or otherwise abnormal fluid levels in the human body.

The microstrip antennae included a ceramic material coated with thin layers of copper for the resonant structure and ground plane as described above in connection with FIGS. 6 and 7A-7E. As known to those skilled in the art, other materials, such as gold or silver, can be used for the resonant structure. The phantom 800 included emulated skin 810, comprising carbon-loaded foam, an emulated fat layer 820, comprising glycerin, and a movable, emulated muscle bundle 830, comprising "Ultravist 370" contrast medium or contrast agent available from Schering AG of Berlin, Germany as illustrated in FIGS. 10 and 11. The emulation materials were chosen to approximate the dielectric properties of the tissues to be emulated.

Figure 12:
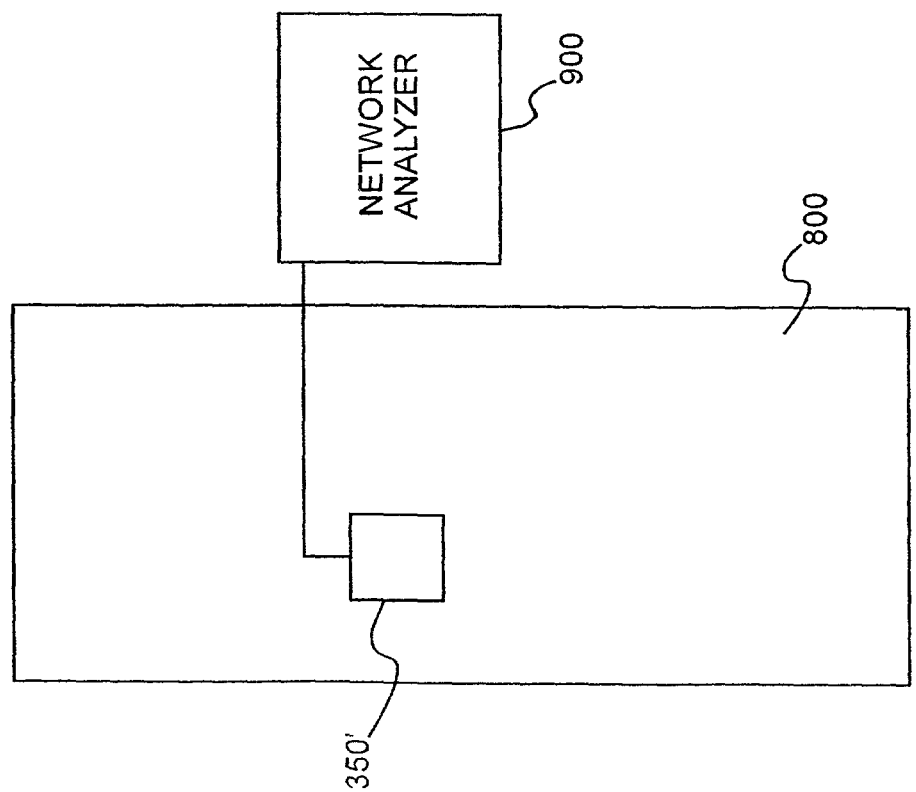
FIG. 12 illustrates an experimental setup in which a single antenna was used as both the transmitter and receiver.
Figure 13:
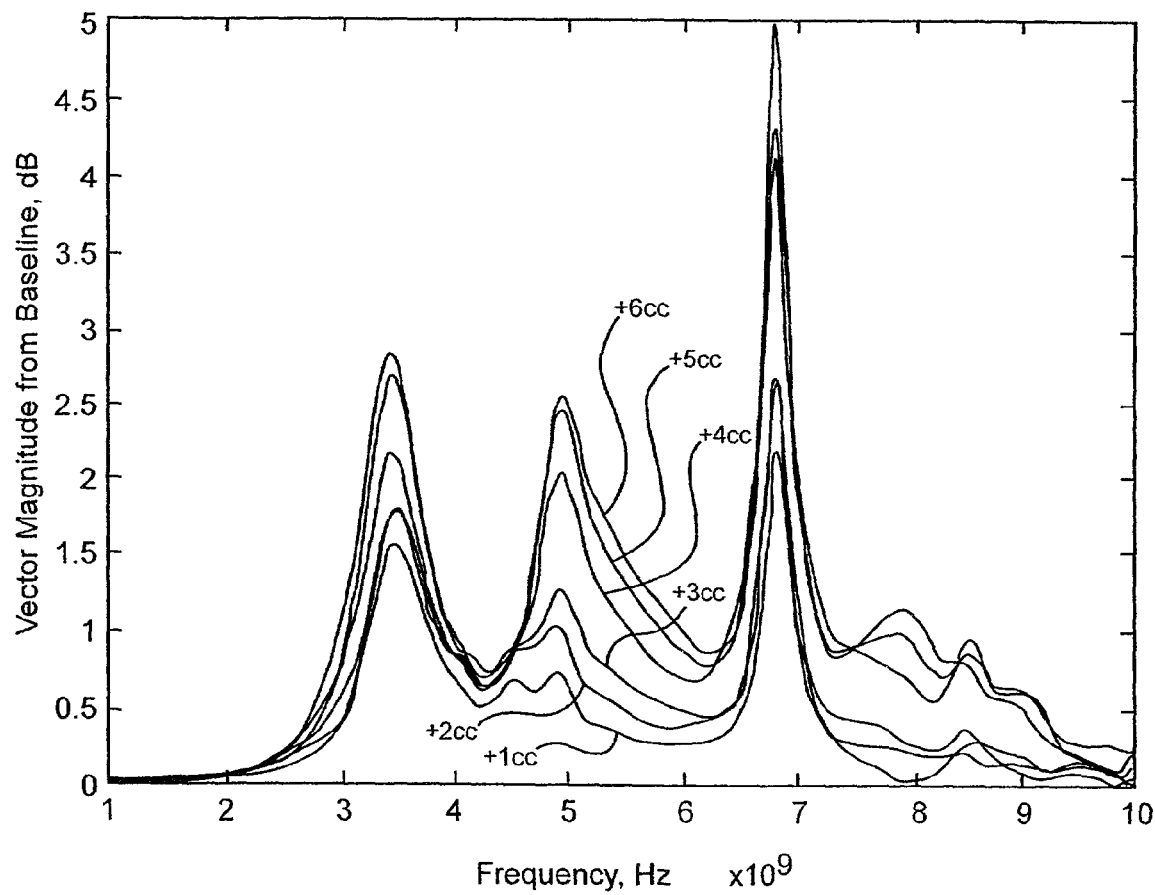
FIG. 13 the effect of increasing fluid level on the received signal in the setup of FIG. 9.

As illustrated in FIGS. 12 and 13, single and dual patch antenna configurations were arranged on the phantom 800. An HP8510C network analyzer 900 was used to generate a source signal and to determine the response of the antenna(e) 350' (see FIG. 6 and description above). Extravasation was emulated by filling a balloon 850 with Ultravist 370 contrast medium. The balloon 850 was filled via tubing 860 in fluid connection with a source of contrast medium (not shown). The thickness of the emulated fat layer 820 in the configuration shown in FIGS. 10 and 11 was approximately 8 mm. The balloon 850 was filled with the contrast agent Ultravist 370 and placed between the muscle bundle 830 and the skin layer 810.

The microstrip patch antennae 350', 350 were designed to couple efficiently into tissue as described in connection with FIG. 6. By spacing the resonating patch element 370 from the skin layer 810 as illustrated in FIG. 6, one can reduce near-field loading. Furthermore, by using high-permittivity ceramic material in the superstrate 360 to provide this non-conductive spacing and intrinsic impedance matching, energy coupling into tissue can be increased. In these experiments of the sensors of the present invention, the substrate thickness was approximately 2.5 mm and the superstrate thickness was approximately 1.5 mm. The relative permittivity values at 5 GHz for each of the substrate 380 and the superstrate 360 were 10.2 and 20, respectively.

1A. Single Patch Antenna Experiments

In these experiments, a single antenna 350' was applied to phantom 800 generally directly over the extravasation site, i.e., the balloon 850. The configuration is shown in FIG. 12. The emulated skin 810 and the muscle bundle 830 were both in place during these experiments. $S_{11}$ measurements, i.e., microwaves transmitted on a first antenna, port 1, and received on the same antenna, port 1, were made using network analyzer 900 to detect changes in the reflected energy created by the antenna 300. The results from these experiments are shown in FIG. 13. The baseline in the experiments corresponded to having the balloon 850 filled with approximately 1-2 cc of Ultravist 370.

1B. Dual Patch Antenna Experiments

Figure 14:
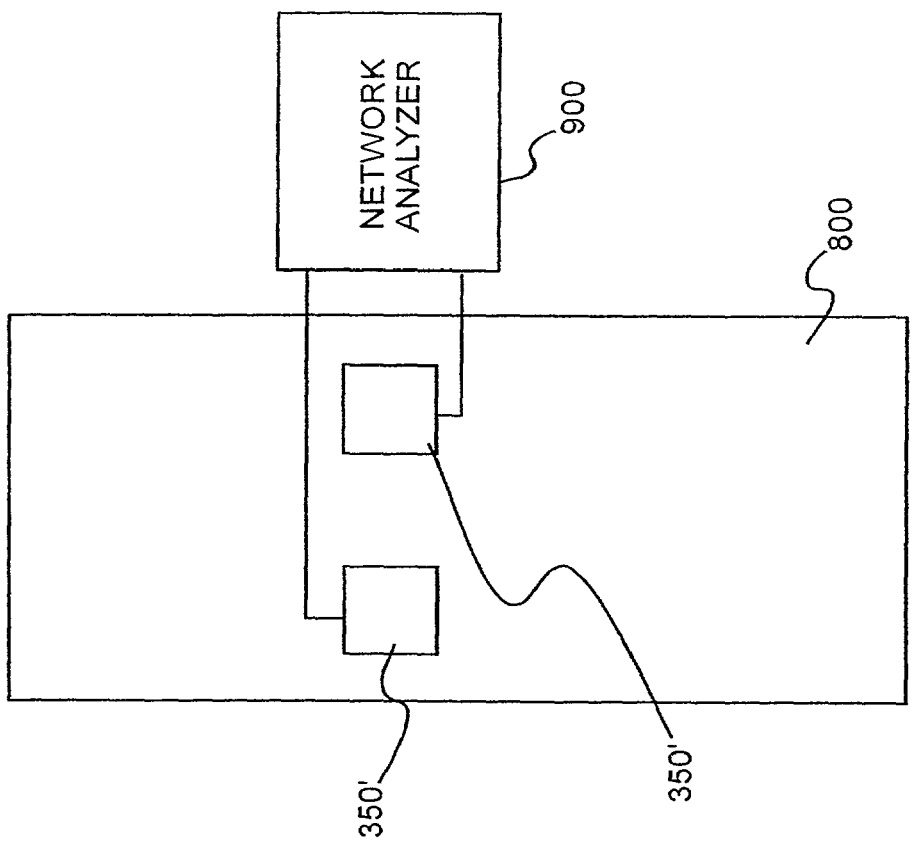
FIG. 14 illustrates an experimental setup in which one antenna was used as a transmitter and another antenna was used as a receiver.
Figure 15:
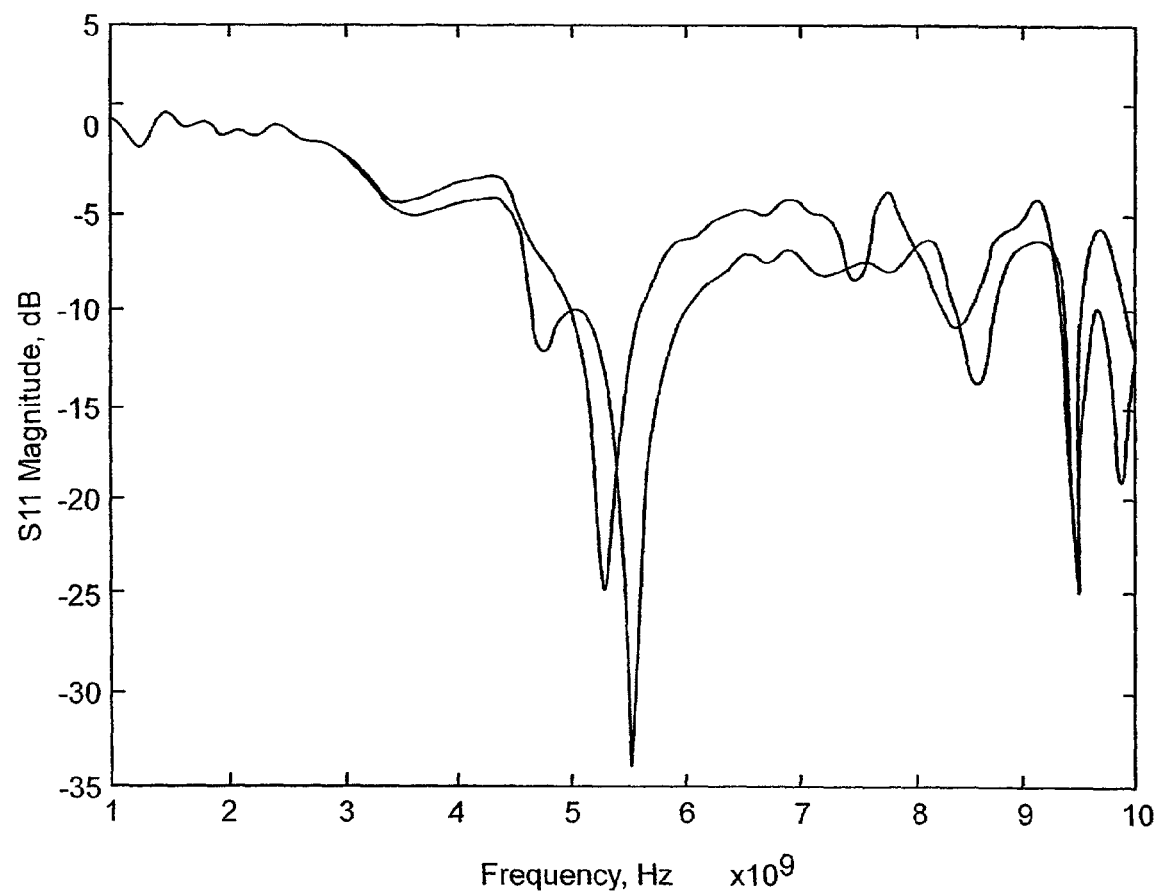
FIG. 15 illustrates a comparison of the resonance frequencies of the two antennae of FIG. 14.

The setup for the dual patch antenna configuration is shown in FIG. 14. First, $S_{11}$ measurements were made with each of the patch antennae 350' to determine if the antennae 350' resonated at similar frequencies and, therefore, coupled effectively. The results of these measurements are shown in FIG. 15. There was overlap in primary resonance modes for each antenna and sufficient $S_{21}$ coupling, i.e., microwaves transmitted on a first antenna, port 1, and received on a second antenna, port 2, occurred, although the match was not optimized and can be readily improved to further increase coupling.

Figure 16:
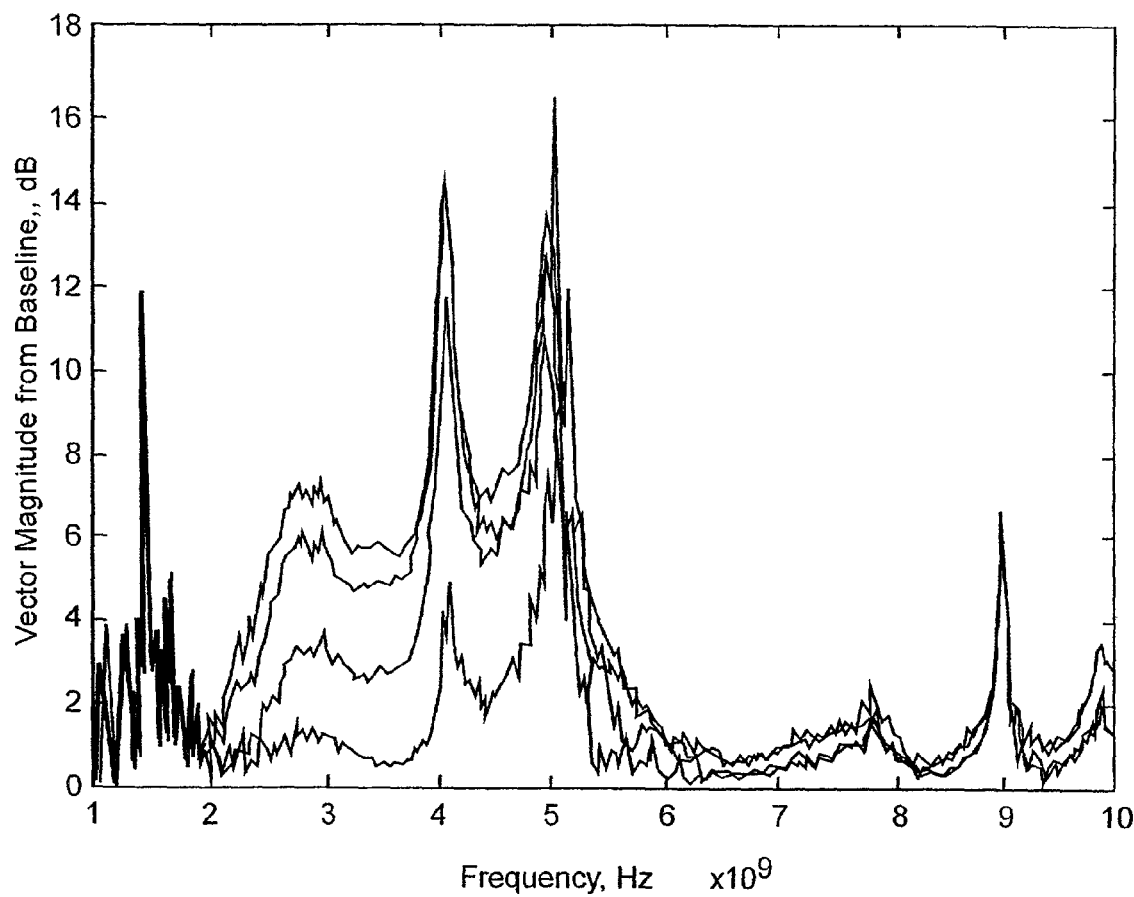
FIG. 16 the effect of increasing fluid level on the received signal in the setup of FIG. 14.

The separation between the substrates 380 of the antennae in the dual patch antenna configuration of FIG. 14 was approximately 1.0 cm, and the separation between active resonant elements 370 was approximately 2.5 cm. As clear to one skilled in the art, the substrate size can be changed, and separation distance can be changed. Parameters such as directionality, tissue coupling, data processing and signal processing were not optimized in these experiments. The results for the dual antenna configuration are shown in FIG. 16. The baseline in this experiment corresponded to having the balloon 850 filled with approximately 1-2 cc of Ultravist 370.

The results of each of the single antenna experiments and the dual antenna experiments indicate that elevated fluid levels are readily detectable using the sensors of the present invention in the detection system of the present application by comparison of a measured signal to a reference signal.

2. Organic Phantom Experiments.

Although the inorganic phantom experiments described above indicate the sensitivity of the sensors of the present invention to even slightly elevated fluid levels, emulation of the "lossy" dielectric nature of human skin using synthetic, inorganic materials is difficult. Thus, further experiments were conducted on organic phantoms to confirm the sensitivity of the sensors of the present invention to elevated or changing fluid levels in organic tissue. In these experiments, chicken skin/tissue was chosen as a model for human skin/tissue on the basis of similarity in permittivity between chicken tissue and human tissue. In general, human skin varies in thickness from approximately 0.6 to 1.0 mm whereas chicken skin is approximately 0.4 mm thick. Experiments were thus performed with chicken phantoms having a single skin layer and a double skin layer, to better emulate human skin.

In several experiments on chicken skin/tissue phantoms, the bowtie sensors 500 were used to measure change during simulated extravasation using Ultravist 370 contrast medium. In several sensors 500 used in the studies leading to the present invention, the spacing between the antennae 400 was approximately 1.5 cm. Inner corner feeds were used to induce circular polarization. The substrate thickness was approximately 2.5 mm. The superstrate thickness, the distance between the resonant patch 410 and the outer surface plateau of the superstrate 420, was approximately 1.25 mm. The resonant structure 410 was square with a side length and width of approximately 8 mm. Margin widths d were approximate 2 mm. Taper angle θ of the superstrate 420 was approximately 30°.

Figure 17:
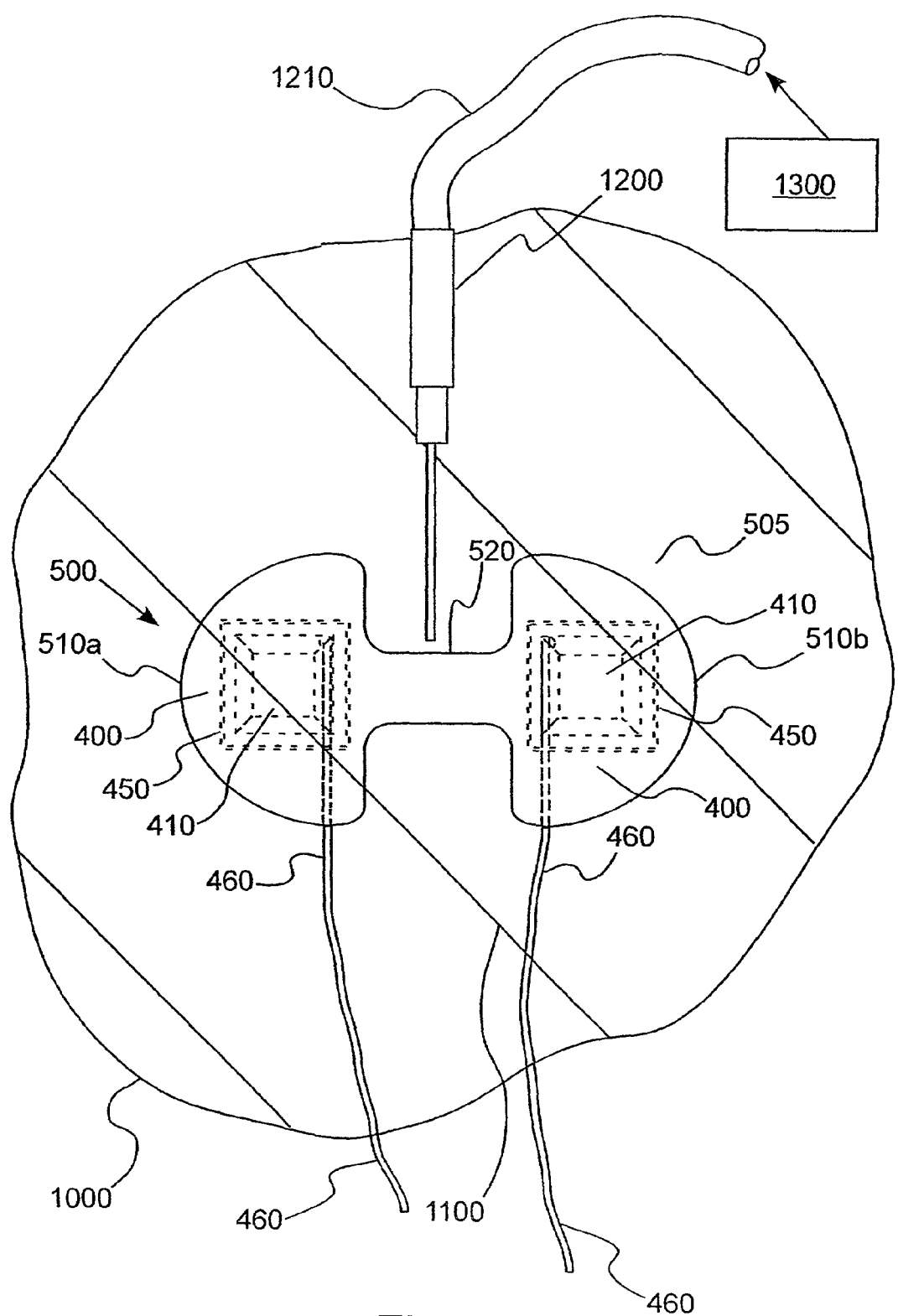
FIG. 17 illustrates the sensor of FIG. 8A in connection with a chicken phantom.

FIG. 17 illustrates attachment of the sensor 500 to a chicken phantom 1000. The chicken phantom 1100 was wrapped tightly in plastic wrap 1100 for purposes of sanitation and to assist in maintaining the shape of the phantom. The sensor 500 was positioned on top of the plastic wrap 1100. Double sided adhesive tape 475, see FIG. 7B, available from 3M under product number/name 1512, was applied to the bottom of the sensor 500 before being coupling to chicken phantom 1000. In some studies, superglue was also placed between the double-sided tape 475 and the plastic wrap 1100. Adhesive tape 575, see FIG. 8D, was placed over the sensor 500 to secure the sensor 500 to the chicken phantom 1000. Ultravist 370 contrast medium was injected/extravasated into chicken phantom 1000 via a catheter 1200 connected to a VISTORON CT® injector 1300 available from Medrad, Inc. of Indianola, Pa. via flexible tubing 1210.

Figure 18:
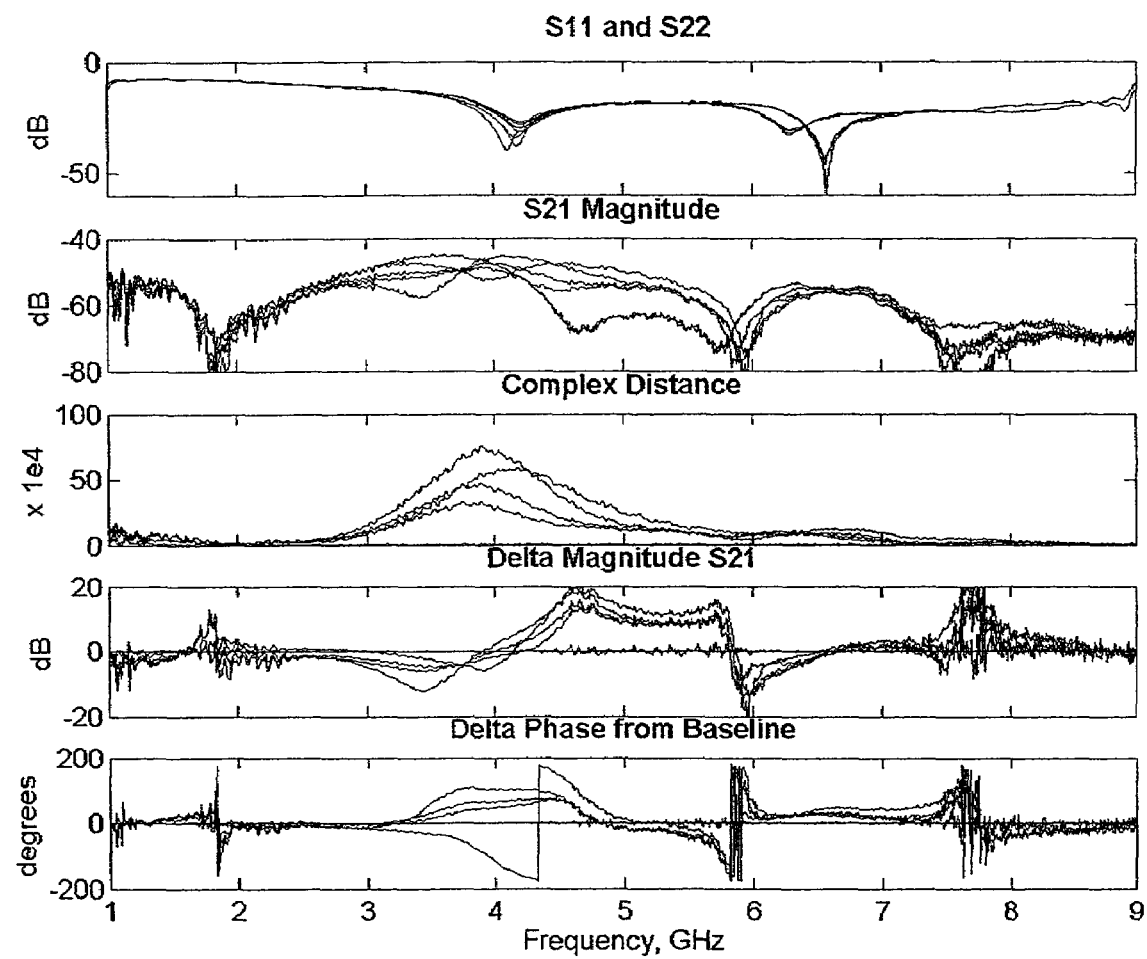
FIG. 18 illustrates signal data resulting from extravasation studies on a single-skinned chicken phantom.

Use of the injector 1300 enabled accurate control of flow rate and volume of injected contrast medium. Contrast medium was injected at a flow rate of 2.5 cc/sec up to a volume of 10 cc. FIG. 18 illustrates data in several forms taken over a frequency range of 1 to 9 Ghz from a single-skin chicken phantom using the sensor 500 as described above. In that regard, FIG. 18 sets forth $S_{11}$ and $S_{22}$ data, i.e., microwaves transmitted on a second antenna, port 2, and received on the second antenna, port 2, $S_{21}$ magnitude data, "complex distance" data, $S_{21}$ delta magnitude data and delta phase from baseline data.

Of the above manners of expressing measured signal data, "complex distance" is believed to provide a direct relationship between extravasated volume and output. Other calculations that exhibit relationships to extravasation or fluid level change include, but are not limited to, changes from the reference (baseline) in $S_{21}$ magnitude and $S_{21}$ phase. FIGS. 19A-19C illustrate "complex distance" as a function of frequency and volume injected in the upper graphs. The lower graphs of FIGS. 19A-19C set forth the maximum "complex distance" over the measured range frequencies as a function of volume.

Figure 20:
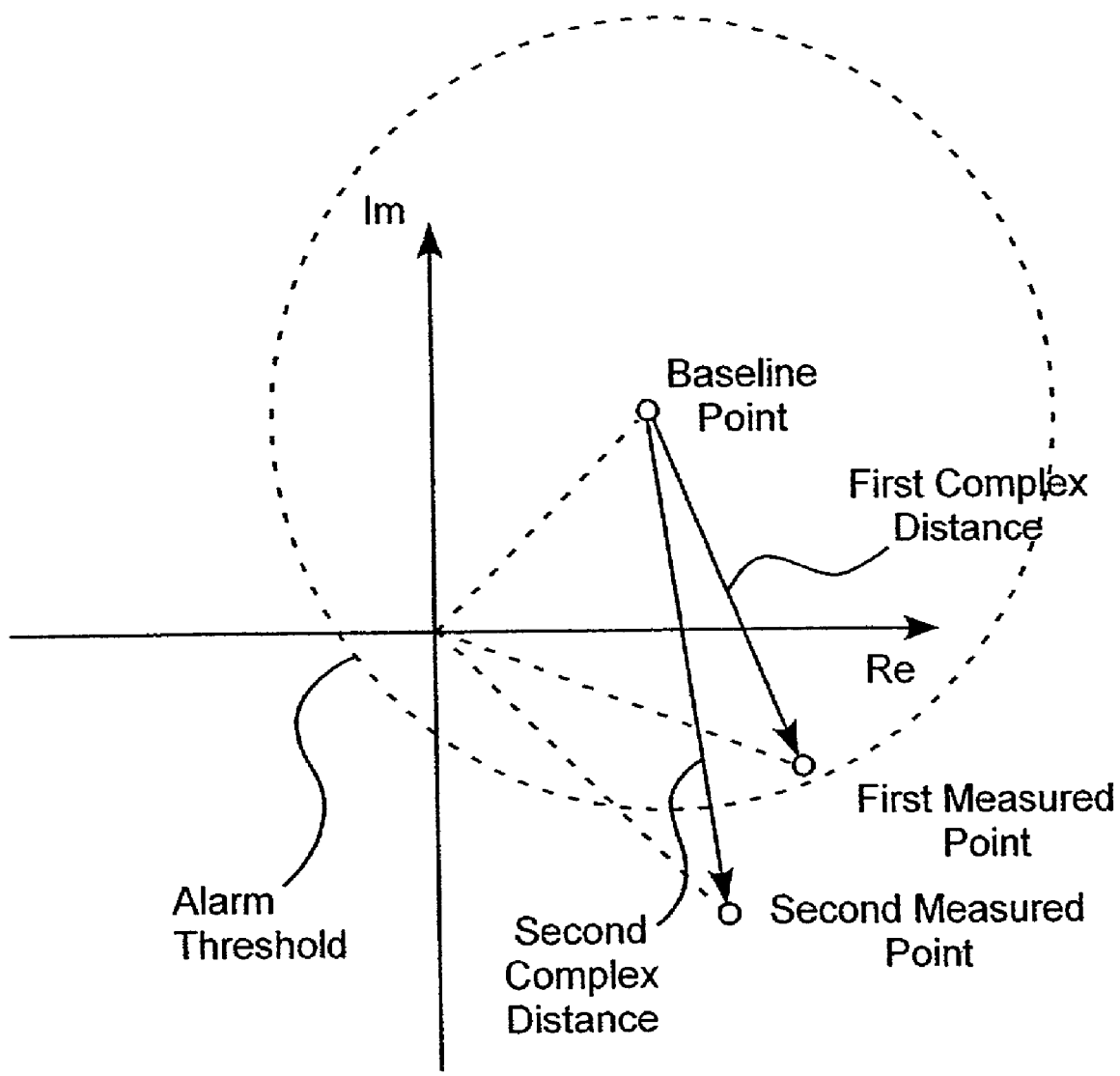
FIG. 20 illustrates a graphical representation of "complex distance".

FIG. 20 provides a graphic illustration of a "complex distance" algorithm used in the studies leading to the present invention for a single frequency. The algorithm utilizes magnitude and phase information and enhances signal processing in frequency regions where signal coupling is strong. In one embodiment of the algorithm, a reference or baseline signal (corresponding to 0 cc of injected contrast medium, for example) is first measured at each frequency or band of frequencies to be investigated. The magnitude and phase data are converted to complex form, i.e., x+yi, and processed as illustrated by FIG. 20, wherein the complex data points are plotted on a complex plane having its abscissa as the real (Re) part, x, and its ordinate as the imaginary (Im) part, y. The reference or baseline magnitude and phase measurements thus become points in the complex plane. The magnitude and phase for measured data points are similarly converted to complex form and also plotted on the complex plane to become measured data points. The scalar distance between each baseline point and each measured data point at the corresponding frequency is determined and each of these distances are referred to herein as a "complex distance," see FIG. 20.

An alarm threshold can be defined for each frequency so that a plurality of alarm thresholds corresponding to the frequencies of the range of frequencies of interest can be defined. Each given alarm threshold forms a circle around a baseline point having a radius of some pre-determined value that is above levels caused by random noise or normal motion disturbances corresponding to the alarm threshold, see the dashed circular line forming an alarm loci in FIG. 20. The reference or baseline points can be reestablished as necessary during use of a sensor.

Rather than compare each point of measured data to a baseline point, as suggested by FIG. 20, it is also possible to determine a complex baseline curve across a given range of frequencies and also a "complex distance" curve across the same given range of frequencies. The area under the "complex distance" curve can then be determined and compared to a pre-determined threshold value that is above levels caused by random noise or normal motion disturbances. More particularly, for this embodiment, the calculation of the area under the "complex distance" curve across a frequency range of interest yields one number that is compared to a reference or baseline number that can be found with the same technique, i.e., by calculating the area under a reference or baseline curve across the frequency range of interest.

In other words, the "complex distances" at the various frequencies are calculated. At that step, instead of comparing each "complex distance" to the threshold at that point, one integrates all of the "complex distances" in the frequency range of interest, providing the area under the curve. The resultant value is compared to a threshold number corresponding to the area under the reference or baseline curve across the frequency range of interest. Under the algorithm illustrated in FIG. 20, a single "complex distance" at some frequency crossing the threshold can trigger an alarm. In the case of comparison of integrated areas, however, a sufficiently strong single "complex distance" or a group of such "complex distances" are required to create a sum/integral that exceeds a threshold value. It is also possible, for example, to accumulate individual "complex distance" comparisons with their corresponding thresholds and determine that an alarm will be indicated only if a predetermined number of the "complex distances" have exceeded their thresholds.

It has been found that variations in the measurement signals occur among different humans and among different anatomical sites on the same human for the same level of extravasation. Thus, for a given volume of extravasation in, for example, two different tissue anatomies, the "complex distance" calculation may yield significantly different values. To correct for such differences, the baseline or reference $S_{21}$ magnitude curves are normalized by multiplying every point in the reference $S_{21}$ curve to force the peak value (or area under the curve) to equal one and then multiplying all subsequent measurement curves, curves created during actual operation of the detection system, by the same factor. Such normalization has been found to make the "complex distance" values more consistent when similar subcutaneous tissue changes occur in two different human subjects or in two different anatomical sites on the same human.

FIGS. 19A and 19B correspond to experiments with double skin chicken phantoms 1000, while FIG. 19C corresponds to an experiment with a single skin chicken phantom 1000. The data of FIG. 18 and FIG. 19C are taken from the same experiment.

In FIG. 19A a gradual signal increase is observed as the volume of injected contrast medium increases. In FIG. 19B, a signal plateau is reached at injection of approximately 2 cc of contrast medium, indicative of signal saturation in the field of the sensor. In FIG. 19C, the signal increases to a maximum at approximately 4 cc of injected contrast medium and then subsequently decreases as more contrast medium is injected. It is believed, that tissue rupture may have led to dissipation of contrast medium from the tissue in the field of the sensor 500 in the experiment of FIGS. 18 and 19C. FIGS. 19A through 19C indicate that the sensors of the present invention are sensitive to even small volumes of fluid in organic tissue. Moreover, it is possible that even information regarding the nature of, for example, an extravasated bolus of fluid can be provided by the sensors of the present invention. In that regard, the shape of the "complex distance" curve can, for example, indicate whether the fluid is pooled in the field of the sensor or dissipated therefrom.

3. Human Subject Experiments.

The sensor 500 was also studied in several experiments with human subjects. In several such studies, signal output was measured at six different sites, for example side, abdominal, and upper forearm areas, having varying fat layer thicknesses as determined by skin fold measurements. Such measurements indicated fat layers of 2.5, 3.0, 4.0, 5.0, 8.0 and 12.0 mm.

Figure 21A:
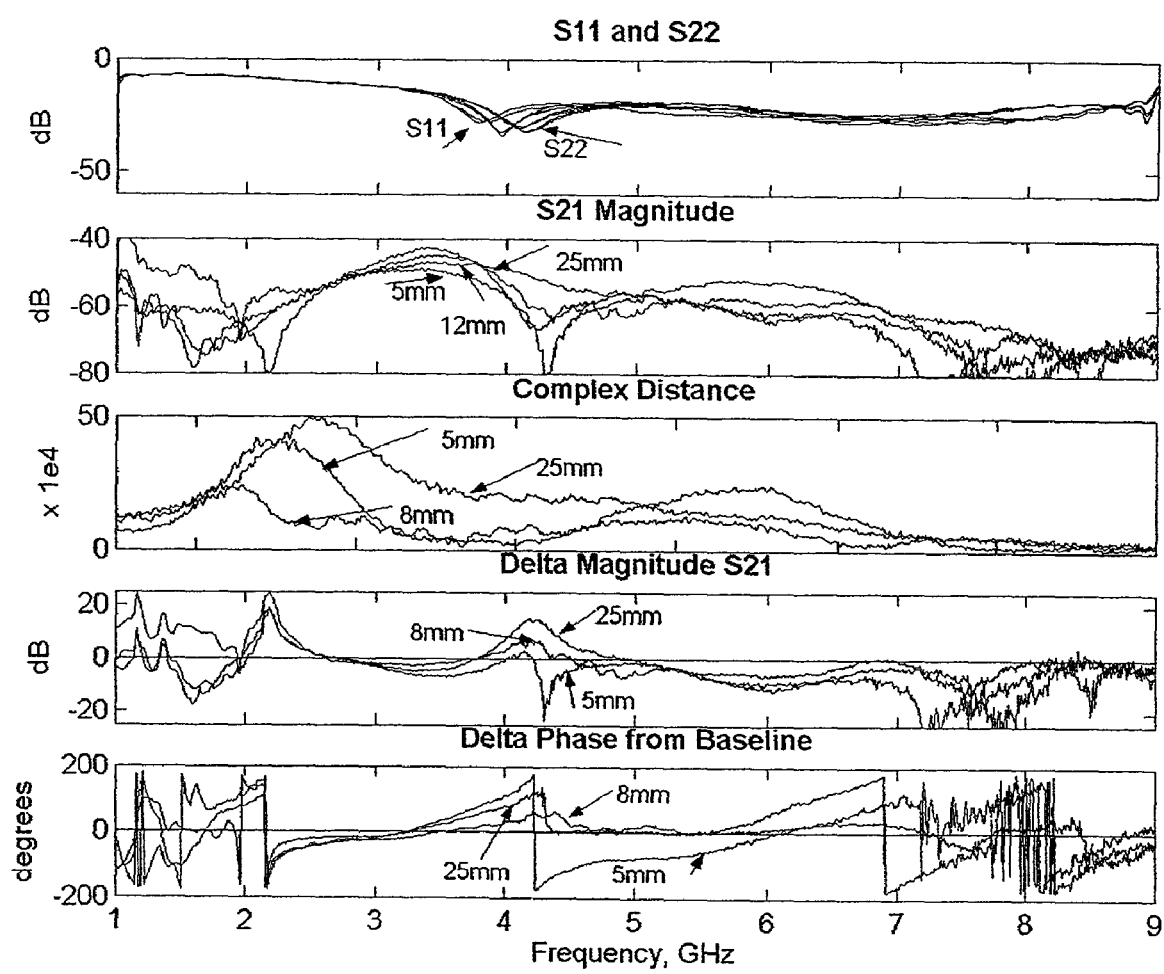
FIG. 21A illustrates signal data resulting from studies using the sensor of FIG. 8A on a human subject on areas of varying fat layer thickness.
Figure 21B:
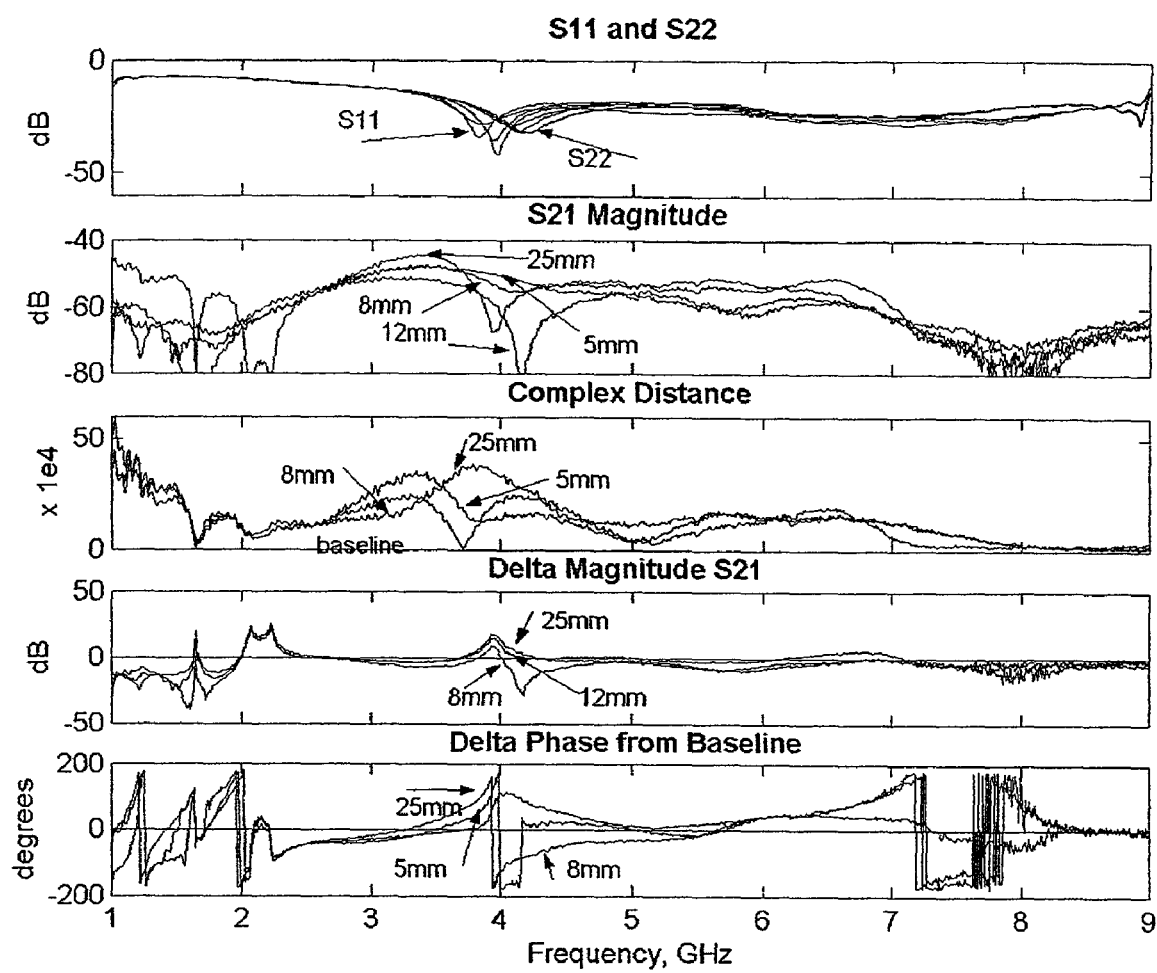
FIG. 21B illustrates signal data resulting from studies using the sensor of FIGS. 8A on another human subject on areas of varying fat layer thickness.

FIGS. 21A and 21B set forth $S_{11}$ and $S_{22}$ data, $S_{21}$ magnitude data, "complex distance" data, $S_{21}$ delta magnitude data and delta phase from baseline data for each of the fat layer thicknesses over a frequency range of approximately 1 to 9 GHZ in two studies. The data demonstrate good skin and fat penetration of the energy of the sensor 500 into human tissue at all the fat thicknesses studied.

The effect of patient motion on the output signal of the sensor 500 was also studied. In these experiments, the underside of the sensor 500, including the antennae 400, was covered with double-sided adhesive tape 475 as illustrated in connection with FIG. 7A. In several experiments, the double-sided tape was then placed in direct contact with the patients skin in the area of the antecubital fossa. Adhesive tape 575 was then placed over the sensor 500. The subject's arm was strapped in a jig to limit certain arm movements and the subject was led through six different arm position. In position 1 or the baseline position, the subject extended his or her arm to a straight position with the palm open and facing inward. In position 2, the subject clenched his or her fist. In position 3, the subject bent his or her elbow approximately 45° inward and opened his or her hand. In position 4, the subject maintained the elbow angle of position 3 and clenched his or her fist. In position 5, the subject maintained the elbow angle of positions 3 and 4 and supanated the wrist. In position 6, the arm was straightened and the wrist flexed.

Figure 22A:
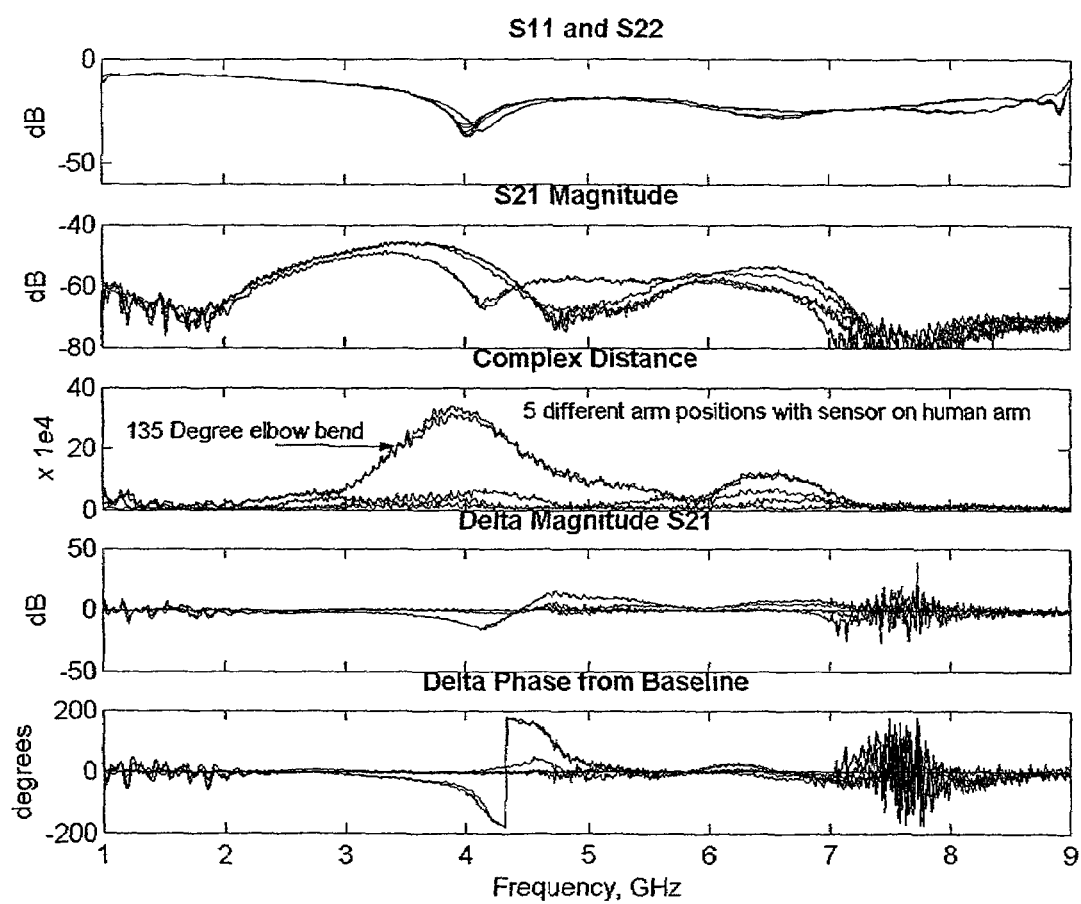
FIG. 22A illustrates signal data resulting from studies using the sensor of FIG. 8A on a human subject's arm at various arm positions.
Figure 22B:
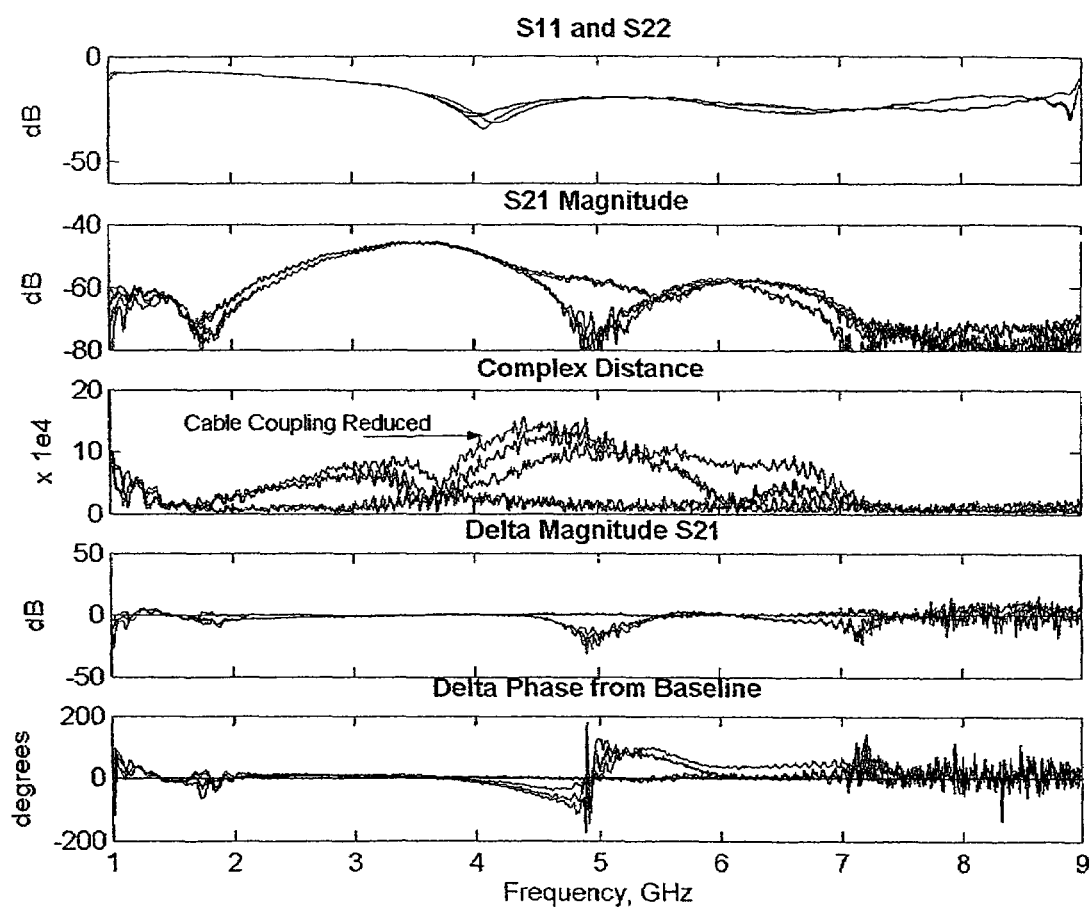
FIG. 22B illustrates signal data resulting from studies using the sensor of FIG. 8A on a human subject's arm at various arm positions wherein sensor cables were maintained in separation.

FIGS. 22A and 22B set forth $S_{11}$ and $S_{22}$ data, $S_{21}$ magnitude data, "complex distance" data, $S_{21}$ delta magnitude data and delta phase from baseline data for each of the above positions over a frequency range of approximately 1 to 9 GHZ in two studies. The data demonstrate that the effect of patient motion on the output signal or motion artifact is not large as compared to the signal effect of fluid introduction found in the phantom studies. Thus, motion artifacts will not present a substantial problem in, for example, detection of extravasation, and the effects of such artifacts can be further reduced via data manipulation such as averaging. In the studies of FIG. 22B, precaution was taken to prevent contact and excessive motion of the cable leads to the antennae 400. Such precautions were found to decrease motion artifacts as compared to the studies of FIG. 22A. It was determined that stray energy transfer traveling on the outside of the cables or crosstalk can cross from one cable to the other and back down to the opposite antenna(e). In this scenario, the motion of the cables will impact this stray energy and therefore its impact on the measurement signal. Furthermore, stray energy emitted by the transmitting antenna(e) can be reflected by nearby moving body parts such that the amount of stray energy scattered to the receiving antenna(e) can vary and impact the measured signal. Techniques such as proper shielding to minimize stray energy leakage and reception are therefore desirable. In addition to preventing contact and excessive motion of cable leads, it is also possible to user wireless transmission to reduce artifact.

Although the present invention has been described in detail in connection with the above embodiments and/or examples, it is to be understood that such detail is solely for that purpose and that variations can be made by those skilled in the art without departing from the invention. The scope of the invention is indicated by the following claims rather than by the foregoing description. All changes and variations which come within the meaning and range of equivalency of the claims are to be embraced within their scope.

The invention claimed is:

1. A sensor element for injecting and/or receiving electromagnetic waves into body tissue, said sensor comprising:
   a housing having a bottom and at least one side wall;
   a substrate mounted within said bottom and at least one side wall;
   a superstrate mounted to said substrate and having a base facing said substrate and an outer surface extending away from said substrate, said outer surface having a transitional periphery interconnecting said base to an outer surface plateau extending over at least a central portion of said superstrate; and
   a generally planar antenna element accommodated by and mounted between said substrate and said superstrate, wherein at least a portion of said transitional periphery of said outer surface of said superstrate has a generally smooth transition from said base to said surface plateau.

2. A sensor element as claimed in claim 1 wherein said transitional periphery is generally linear so that said outer surface forms a truncated pyramid.

3. A sensor element as claimed in claim 1 wherein said transitional periphery is curvilinear.

4. A sensor element as claimed in claim 1 wherein said housing comprises a resilient material.

5. A sensor element as claimed in claim 4 wherein said resilient material comprises polyurethane.

6. A sensor element as claimed in claim 1 wherein said planar antenna element comprises a rectangular electrically conductive patch.

7. A sensor element as claimed in claim 6 wherein said planar antenna element is square and is electrically contacted adjacent a corner of said element to generate circularly polarized electromagnetic wave signals.

8. A sensor element as claimed in claim 1 wherein said planar antenna element comprises a generally circular electrically conductive patch.

9. A sensor element as claimed in claim 1 wherein said portion of said transitional periphery of said outer surface of said superstrate having a generally smooth transition from said base to said surface plateau directs electromagnetic waves toward said portion.

10. A sensor element as claimed in claim 1 further comprising an electrically conductive shield around at least a portion of said substrate to form an electrically conductive cavity.

11. A sensor element as claimed in claim 10 wherein a resonance mode of said antenna element is matched to a resonance mode of said cavity so that said antenna element and said cavity resonate together.

12. A sensor element as claimed in claim 11 wherein said antenna element and said cavity are rectangular, said resonance mode of said antenna element corresponds to a diagonal measurement of said antenna element and said resonance mode of said cavity corresponds to a side dimension of said cavity.

13. A sensor element as claimed in claim 12 wherein said antenna element and said cavity are congruent squares.

14. A sensor element as claimed in claim 1 wherein said antenna element is mounted to said substrate and said superstrate is removably mounted to said substrate.

15. A sensor element as claimed in claim 14 wherein said outer surface of said superstrate includes adhesive for securing said sensor element to said body tissue.

16. A sensor element as claimed in claim 1 wherein said outer surface of said superstrate includes adhesive for securing said sensor element to said body tissue.

17. A sensor element as claimed in claim 1 wherein said substrate and said superstrate comprise a high permittivity, low loss material.

18. A sensor element as claimed in claim 17 wherein said superstrate comprises a ceramic material.

19. A sensor element as claimed in claim 17 wherein said superstrate comprises a material with an intrinsic impedance substantially the same as the surface impedance of tissue into which electromagnetic waves are to be injected and/or from which electromagnetic waves are to be received.

20. A sensor element as claimed in claim 17 wherein said material comprises magnesium calcium titanium dioxide.

21. A sensor element as claimed in claim 1 wherein said generally planar antenna element is secured to said substrate.

22. A sensor element as claimed in claim 21 wherein said base of said superstrate includes an indentation sized to receive said generally planar antenna element.

23. A sensor element as claimed in claim 22 wherein said indentation in said substrate is formed to accommodate an electrical connection to said generally planar antenna element.

24. A sensor comprising at least two sensor elements each sensor element comprising:
   a substrate;
   a superstrate mounted to said substrate and having a base facing said substrate and an outer surface extending away from said substrate, said outer surface having a transitional periphery interconnecting said base to an outer surface plateau extending over at least a central portion of said superstrate;
   a generally planar antenna element accommodated by and mounted between said substrate and said superstrate, wherein at least a portion of said transitional periphery of said outer surface of said superstrate has a generally smooth transition from said base to said surface plateau; and
   a housing having a bottom and at least one side wall, wherein said at least two sensor elements is supported within said bottom and side wall.

25. A sensor as claimed in claim 24 wherein said housing comprises a resilient material.

26. A sensor as claimed in claim 25 wherein said resilient material comprises polyurethane.

27. A sensor as claimed in claim 24 wherein said housing is shaped and said sensing elements are positioned within said housing to permit visual observation and palpation of body tissue interposed between said at least two sensor elements.

28. A sensor as claimed in claim 27 wherein said housing is shaped like a bowtie having two expanded portions interconnected by a portion more narrow than said expanded portions, each of said two expanded portions having at least one sensor element housed therein.

29. A sensor as claimed in claim 27 wherein said housing having first and second elongated portions interconnected by a third elongated portion, each of said first and second elongated portions having at least one sensor element housed therein.

30. A sensor as claimed in claim 29 wherein said third elongated portion is positioned at one end of said two elongated portions so that said sensor housing is generally U-shaped to permit visual observation and palpation of body tissue interposed within the open end of said U-shaped housing.

31. A sensor as claimed in claim 29 wherein said portion of said transitional periphery of at least one of said at least two sensor elements is positioned to provide directional transmission and/or receipt of electromagnetic wave energy.

32. A sensor as claimed in claim 31 wherein said transitional periphery of at least two of said at least two sensor elements are positioned to be directed toward one another.

33. A sensor as claimed in claim 24 comprising at least four sensor elements, said at least four sensor elements defining at least two electromagnetic wave transmitters and at least two of said sensor elements defining at least two electromagnetic wave receiver elements, said at least two electromagnetic wave transmitters being positioned opposite said at least two electromagnetic wave receivers.

34. A sensor as claimed in claim 33 wherein said portions of said transitional periphery of said at least two electromagnetic wave transmitters is positioned toward said at least two electromagnetic wave receivers.

35. A sensor as claimed in claim 34 wherein said portions of said transitional periphery of said at least two electromagnetic wave receivers is positioned toward said at least two electromagnetic wave transmitters.

36. A sensor as claimed in claim 24 wherein said at least two electromagnetic wave transmitters are separated from said at least two electromagnetic wave receivers by body tissue to be monitored by electromagnetic waves.

37. A sensor as claimed in claim 24 wherein said planar antenna elements of said at least two sensor elements are square and are electrically contacted adjacent inner corners of said elements.

38. A sensor comprising at least two sensor elements each sensor element comprising:
   a first substrate;
   a second substrate; and
   a generally planar antenna element accommodated by and mounted between said first substrate and said second substrate, wherein said antenna element is structured to emit electromagnetic waves from an edge of the antenna and said at least two sensor elements are angularly oriented relative to and directed toward each other.

39. A sensor as claimed in claim 38 wherein said angular orientation of said at least two sensors is approximately 120° relative to each other.

40. A sensor as claimed in claim 38 wherein said angular orientation of said at least two sensor elements are adjustable relative to each other.

41. A sensor comprising at least two sensor elements each sensor element comprising:
   a substrate;
   a superstrate mounted to said substrate and having a base facing said substrate and an outer surface extending away from said substrate;
   a generally planar antenna element accommodated by and mounted between said substrate and said superstrate; and
   a housing supporting said at least two sensor elements to maintain a predetermined distance between said at least two sensor elements, wherein said housing includes a bottom and at least one side wall such that said at least two sensor elements are support therewithin.

42. A sensor as claimed in claim 41 wherein said housing comprises a resilient material.

43. A sensor as claimed in claim 41 wherein said resilient material comprises polyurethane.

44. A sensor as claimed in claim 41 wherein said housing is shaped and said sensing elements are positioned within said housing to permit visual observation and palpation of body tissue interposed between said at least two sensor elements.

45. A sensor as claimed in claim 44 wherein said housing is shaped like a bowtie having two expanded portions interconnected by a portion more narrow than said expanded portions, each of said two expanded portions having at least one sensor element housed therein.

46. A sensor as claimed in claim 44 wherein said housing having first and second elongated portions interconnected by a third elongated portion, each of said first and second elongated portions having at least one sensor element housed therein.

47. A sensor as claimed in claim 46 wherein said third elongated portion is positioned at one end of said two elongated portions so that said sensor housing is generally U-shaped to permit visual observation and palpation of body tissue interposed within the open end of said U-shaped housing.

48. A sensor as claimed in claim 41 comprising at least four sensor elements, said at least four sensor elements defining at least two electromagnetic wave transmitters and at least two of said sensor elements defining at least two electromagnetic wave receiver elements, said at least two electromagnetic wave transmitters being positioned opposite said at least two electromagnetic wave receivers.

49. A sensor as claimed in claim 41 wherein said at least two electromagnetic wave transmitters are separated from said at least two electromagnetic wave receivers by body tissue to be monitored by electromagnetic waves.

50. A sensor as claimed in claim 41 wherein said planar antenna elements of said at least two sensor elements are square and are electrically contacted adjacent inner corners of said elements.

51. A sensor element for injecting and/or receiving electromagnetic waves into body tissue, said sensor comprising:
   a housing having a bottom and at least one side wall;
   a substrate mounted within said bottom and said at least one side wall; and
   a superstrate mounted to said substrate and having a base facing said substrate and an outer surface facing away from said substrate; and
   a generally planar antenna element accommodated by and mounted between said substrate and said superstrate, wherein said housing extends to said outer surface of said superstrate and an electrical shield surrounds said sensor element except for said outer surface of said superstrate.

52. A sensor element as claimed in claim 51 wherein said housing is flush with said outer surface of said substrate.

53. A sensor element as claimed in claim 51 wherein said housing is recessed below said outer surface of said superstrate and defines a transitional periphery interconnecting said housing to said outer surface of said superstrate, wherein at least a portion of said transitional periphery has a generally smooth transition from said base to said surface plateau.

54. An injection system comprising:
   (a) an injector to inject a fluid into a vascular structure in a body; and
   (b) a sensor element for at least one of transmitting into tissue of the body and receiving therefrom electromagnetic waves for use in ascertaining whether a level of the fluid in the tissue outside the vascular structure has changed, said sensor element comprising:
      (i) a housing having a bottom and at least one side wall;
      (ii) a substrate mounted within said bottom and said at least one side wall;
      (iii) a superstrate mounted to said substrate and having a base facing said substrate and an outer surface extending away from said substrate, said outer surface having a transitional periphery interconnecting said base to an outer surface plateau extending over at least a central portion of said superstrate and enabling said sensor element to be placed in substantial contact with the tissue of the body; and
      (iv) a generally planar antenna element accommodated by and mounted between said substrate and said superstrate, wherein at least a portion of said transitional periphery of said outer surface of said superstrate has a generally smooth transition from said base to said surface plateau.

55. A system for injecting a fluid into a body, the system comprising:
   (a) a pressurizing chamber in which the fluid is pressurized for injection into a vascular structure of the body; and
   (b) a sensor for use in ascertaining whether a level of the fluid in bodily tissue outside the vascular structure has changed, said sensor comprising at least two sensor elements each of which including:
      (i) a substrate;
      (ii) a superstrate mounted to said substrate and having a base facing said substrate and an outer surface extending away from said substrate, said outer surface having a transitional periphery interconnecting said base to an outer surface plateau extending over at least a central portion of said superstrate and enabling said sensor element to be placed in substantial contact with the bodily tissue; and
      (iii) a generally planar antenna element accommodated by and mounted between said substrate and said superstrate, wherein at least a portion of said transitional periphery of said outer surface of said superstrate has a generally smooth transition from said base to said surface plateau.

56. A system for injecting a fluid into a body, the system comprising:
   (a) a pressurizing chamber in which the fluid is pressurized for injection into a vascular structure of the body; and
   (b) a sensor comprising at least two sensor elements oriented angularly relative to and directed toward each other for use in ascertaining whether a level of the fluid in bodily tissue outside the vascular structure has changed, each of said sensor elements including:
      (i) a first substrate;
      (ii) a second substrate; and
      (iii) a generally planar antenna element accommodated by and mounted between said first substrate and said second substrate, wherein said antenna element is structured to emit electromagnetic waves from an edge of said antenna element.

57. An injection system comprising:
   (a) an injector to inject a fluid into a vascular structure in a body; and
   (b) a sensor for use in determining if a level of the fluid in bodily tissue outside the vascular structure has changed, said sensor comprising:
      (i) at least two sensor elements each of which including:
         (A) a substrate;
         (B) a superstrate mounted to said substrate, said superstrate having a base facing said substrate and an outer surface extending away from said substrate that enables said sensor element to be placed in substantial contact with the bodily tissue; and
         (C) a generally planar antenna element accommodated by and mounted between said substrate and said superstrate; and
      (ii) a housing supporting said at least two sensor elements to maintain a predetermined distance between said at least two sensor elements, wherein said housing includes a bottom and at least one side wall such that said at least two sensor elements are support therewithin.

58. An injection system comprising:
   (a) an injector to inject a fluid into a vascular structure of a body; and
   (b) a sensor element for at least one of transmitting into tissue of the body and receiving therefrom electromagnetic waves for use in determining if a level of the fluid in the tissue outside the vascular structure has changed, said sensor element comprising:
      (i) a housing having a bottom and at least one side wall;
      (ii) a substrate mounted within said bottom and said at least one side wall; and
      (iii) a superstrate mounted to said substrate, said superstrate having a base facing said substrate and an outer surface facing away from said substrate for enabling said sensor element to be placed in substantial contact with the tissue; and
      (iv) a generally planar antenna element accommodated by and mounted between said substrate and said superstrate, wherein said housing extends to said outer surface of said superstrate and an electrical shield surrounds said sensor element except for said outer surface of said superstrate.

* * * * *

UNITED STATES PATENT AND TRADEMARK OFFICE
CERTIFICATE OF CORRECTION

PATENT NO. : 7,591,792 B2
APPLICATION NO. : 10/205775
DATED : September 22, 2009
INVENTOR(S) : Bouton It is certified that error appears in the above-identified patent and that said Letters Patent is hereby corrected as shown below:

ON THE COVER PAGE

On Page 2, item (56), under "OTHER PUBLICATIONS", in Column 2, Line 40, delete "40" and insert -- 40, --, therefor.

On Page 2, item (56), under "OTHER PUBLICATIONS", in Column 2, Line 44, delete "39" and insert -- 39, --, therefor.

In Column 13, Line 24, delete "MgCaTiO2." and insert -- $MgCaTiO_2$. --, therefor.

In Column 13, Line 54, delete "MgCaTiO2," and insert -- $MgCaTiO_2$, --, therefor.

In Column 15, Lines 52-53, delete "subject patient" and insert -- subject/patient --, therefor.

In Column 16, Line 21, delete "510beach" and insert -- 510b each --, therefor.

In Column 18, Line 11, delete "Ghz." and insert -- GHz. --, therefor.

In Column 20, Line 29, delete "Ghz" and insert -- GHz --, therefor.

In Column 22, Line 27, delete "GHZ" and insert -- GHz --, therefor.

In Column 22, Line 52, delete "GHZ" and insert -- GHz --, therefor.

In Column 24, Lines 64-65, in Claim 27, delete "palpation of body tissue" and insert -- Palpation of a body tissue --, therefor.

In Column 25, Lines 39-40, in Claim 36, delete "by body tissue" and insert -- by a body tissue --, therefor.

Signed and Sealed this
Eighteenth Day of September, 2012

David J. Kappos
*Director of the United States Patent and Trademark Office*

CERTIFICATE OF CORRECTION (continued)
U.S. Pat. No. 7,591,792 B2

In Column 25, Line 57, in Claim 39, delete "sensors" and insert -- sensor elements --, therefor.

In Column 26, Lines 15-16, in Claim 44, delete "of body tissue" and insert -- of a body tissue --, therefor.

In Column 26, Lines 42-43, in Claim 49, delete "by body tissue" and insert -- by a body tissue --, therefor.

In Column 27, Lines 6-7, in Claim 54, delete "into tissue of the body" and insert -- into a tissue of the body --, therefor.

In Column 27, Line 33, in Claim 55, delete "in bodily tissue" and insert -- in a bodily tissue --, therefor.

In Column 28, Line 2, in Claim 56, delete "in bodily tissue" and insert -- in a bodily tissue --, therefor.

In Column 28, lines 37-38, in Claim 58, delete "into tissue of the body" and insert -- into a tissue of the body --, therefor.